US012715895B2

(12) United States Patent
Mastalerz et al.

(10) Patent No.: US 12,715,895 B2
(45) Date of Patent: Aug. 25, 2026

(54) SULFUR EXTRUSION FROM DISULFIDES BY CARBENES

(71) Applicant: UNIVERSITÄT HEIDELBERG, Heidelberg (DE)

(72) Inventors: Michael Mastalerz, Dossenheim (DE); Alexander Pascal Galow, Weinheim (DE)

(73) Assignee: UNIVERSITÄT HEIDELBERG, Heidelberg (DE)

(*) Notice: Subject to any disclaimer, the term of this patent is extended or adjusted under 35 U.S.C. 154(b) by 766 days.

(21) Appl. No.: 17/906,771

(22) PCT Filed: Apr. 22, 2021

(86) PCT No.: PCT/EP2021/060568
§ 371 (c)(1),
(2) Date: Sep. 20, 2022

(87) PCT Pub. No.: WO2021/214243
PCT Pub. Date: Oct. 28, 2021

(65) Prior Publication Data

US 2023/0151054 A1 May 18, 2023

(30) Foreign Application Priority Data

Apr. 22, 2020 (EP) .................................... 20170862

(51) Int. Cl.
*C07K 1/113* (2006.01)

(52) U.S. Cl.
CPC ................................. *C07K 1/1133* (2013.01)

(58) Field of Classification Search
USPC ........................................................... 568/38
See application file for complete search history.

(56) References Cited

U.S. PATENT DOCUMENTS

2013/0158274 A1 6/2013 Maliverney et al.

OTHER PUBLICATIONS

International Search Report and Written Opinion dated Jul. 13, 2021 issued in International Patent Application No. PCT/EP2021/060568.
Shlomo et al., "Cobalt Carbonyl Catalyzed Reactions of Disulfides: Carbonylation to Thioesters and Desulfurization to Sulfides", Tetrahedron Letters, (1985), vol. 26, No. 22, pp. 2609-2612.
Harpp et al., "Organic Sulfur Chemistry. X. Selective Desulfirization of Disulfides. Scope and Mechanism", Journal of the American Chemical Society, (1971), vol. 93, No. 10, pp. 2437-2445.
Dhar, Preeti et al., "Novel Alkylation with Tetrathiotungstates and Tetrathiomolybdates: Facile Synthesis of Disulfides from Alkyl Halides," J. Org. Chem., 1989, vol. 54, vol. 13, pp. 2998-3000.
Mampuys, Pieter et al., "Iodine-Catalyzed Synthesis of Secondary Thiocarbamates from Isocyanides and Thiosulfonates," Org. Lett., 2016, vol. 18, pp. 2808-2811.
Overberger, C.G. et al., "Cyclic Sulfones. Preparation of 2,5-Di-Chalophenyl)-3, 4-Dihydroxythiophene-1-Dioxides," J. Am. Chem. Soc., 1953, vol. 75, pp. 2075-2077.
Sohn, Chang Ho et al., "Probing the Mechanism of Electron Capture and Electron Transfer Dissociation Using Tags with Variable Electron Affinity," J. Am. Chem. Soc., 2009, vol. 131, No. 15, pp. 5444-5459.
Wolfe, Derek M et al., "Oxidative Desulfurization of Azole-2-Thiones with Benzoyl Peroxide: Syntheses of Ionic Liquids and Other Azolium Salts," Eur. J. Org. Chem., 2007, pp. 2825-2838.
Buchwald, Stephen et al., "Kinetics and Substituent Effects in the Formation of Zirconocene Thioaldehyde Complexes: β-Hydride Elimination Versus Cyclometalation," J. Am. Chem. Soc., 1988, vol. 110, pp. 3171-3175.
Agarwal et al., "Synthesis and Crystal Structures of 2,3,12, 13-Tetralkoxy-21, 23-Dithiaporphyrins and 2,3-Dialkoxy-21-Monothiaporphyrins," Tetrahedon, 2004, vol. 60, pp. 10671-10680.
Bodwell et al., "Nonplanar Aromatic Compounds 5. A Strategy for the Synthesis for cis-10b, 10c-Dimethyl-10b, 10c-Dihydropyrenes., First Crystal Structure of a cis-10b, 10c-Dimethyl-10b, 10c-Dihydrophyrene", J. Am. Chem. Soc., 2001, vol. 123, pp. 4704-4708.
Boekelheide, R.H. Mitchell, V., "Synthesis of Novel Tris-Bridged Cyclophanes. [2.2.2.] (1,3,5,)Cyclophane-1,9,17-Triene," Journal of the American Chemical Society, 1970, vol. 92, No. 11, pp. 3512-3513.
Brooke et al., "The Synthesis and Rearrangement Reactions of 2, 3, 4, 5, 6-Pentafluorobenzyl Methyl Sulphoxide and 1, 1-Bis(Pentafluorophenyl)methyl Methyl Sulphoxide," Journal of Fluorine Chemistry, 1988, vol. 41, pp. 263-275.
Buehrdel et al., "Synthesis of New Lipophilic Sulfones and Their Use in Cyclization Reactions", Phosphorus, Sulfur, and Silicon and the Related Elements, 2009, vol. 184, No. 5, pp. 1161-1174.
Collins et al., "A Facile Route to Old and New Cyclophanes via Self-Assembly and Capture," Nature Communications, 2016, vol. 7, No. 11052, pp. 1-7.
Eccles et al., "Convenient and Robust One-Pot Synthesis of Symmetrical and Unsymmetrical Benzyl Thioethers from Benzyl Halides Using Thiourea," 2010, Gen. Pap. Arkivoc, vol. ix, pp. 216-228.
Fritze et al., "Dynamic Disulfide Metathesis Induced by Ultrasound", Chem. Commun., 2016, vol. 52, No. 38, pp. 6363-6366.
Fukase et al., "Total Synthesis of Peptide Antibiotic Nisin," Tetrahedron Letters, 1988, vol. 29, No. 7, pp. 795-798.
Hajipour et al., "Oxidation of Thiols Using K2S208 in Ionic Liquid", Phosphorus Sulfur Silicon Relat. Elem., 2009, vol. 184, No. 7, pp. 1920-1923.
Huang et al., "Base-Controlled Fe(Pc)-Catalyzed Aerobic Oxidation of Thiols for the Synthesis of S—S and S—P(o) Bonds," Org. Biomol. Chem., 2018, vol. 16, pp. 4236-4242.
Liu et al., "Electrophilic Sulfur Transfer Reactions in Organic Synthesis. Preparation for a Diastereomer of the Key Macrocyclic Component of Griseoviridin," J. Org. Chem., 1986, vol. 51, pp. 5332-5337.

(Continued)

*Primary Examiner* — Ana Z Muresan
(74) *Attorney, Agent, or Firm* — McDonnell Boehnen Hulbert & Berghoff LLP

(57) ABSTRACT

The present invention relates to a method for preparing a compound T having a thioether group from a compound D having a disulfide group in the presence of a carbene.

8 Claims, 1 Drawing Sheet

(56) References Cited

OTHER PUBLICATIONS

Mampuys et al., "Iodide-Catalyzed Synthesis of Secondary Thiocarbamates from Isocyanides and Thiosulfonates," Org. Lett., 2016, vol. 18, pp. 2808-2811.
Matake et al., "Phase-Managing Method with Gas Evolution and its Application to Organic Synthesis," Tetrahedron Letters, 2016, vol. 57, pp. 672-675.
Matsumura et al., "Preparation of Imidazolinium Salts by the Pd-Catalyzed Reduction of Thioureas with Triethylsilane and Trialkysilyl Triflate," Tetrahedron Letters, 2014, vol. 55, pp. 1412-1415.
Panduranga et al., "Alternative Protocol for the Synthesis of Symmetrical Dibenzyl Diselenides and Disulfides," Synthesis, 2016, vol. 48, pp. 1711-1718.
Park et al., "Oxidation of Dibenzyl Sulfide via an Oxygen Transfer from Palladium Nitrate," Bull. Korean Chem. Soc., 2006, vol. 27, No. 12, pp. 2023-2027.
Shah et al., "VIS/NIR Light Driven Mild and Clean Synthesis of Disulfides in the Presence of $Cu_2$ (OH)$PO_4$Under Aerobic Conditions", RSC Adv., 2015, vol. 5, pp. 45416-45419.
Ding et al., "Eco-Friendly One-Pot Synthesis of 2,4-Distributed Triazoles by Griding Under Catalyst- and Solvent-Free Conditions—Abstract Only," Phosphorus, Sulfur, and Silicon and the Related Elements, 2001, vol. 186, No. 2, URL: https://www.tandfonline.com/doi/abs/10.1080/10426500802529051, Obtained via Web on Oct. 26, 2022.
Zeynizaden, Benzad, "Oxidative Coupling of Thiols to Disulfides with Iodine in Wet Acetonitrile," J. Chem. Research (S), 2002, pp. 564-566.
International Preliminary Report on Patentability dated Oct. 25, 2022 issued in International Patent Application No. PCT/EP2021/060568.
Xiao, Huilong et al., "An Approach to Disulfides Synthesis Promoted by Aqueous Media," Phosphorus, Sulfur, and Sillicon, 2009, vol. 184, pp. 2553-2559.
Khan, Khalid Mohammed et al., "An Improved Method for Synthesis for Disulfides by Periodic Acid and Sodium Hydrogen Sulfite in Water," Letters in Organic Chemistry, 2010, vol. 7, No. 5, pp. 415-419.
Sousa, et al., "Oxo-Rhenium(V) Complexes Containing Heterocyclic Ligands as Catalysts for the Reduction of Sulfoxides," Eur. J. Org. Chem., 2014, pp. 1855-1859.

D

NHC

T

SULFUR EXTRUSION FROM DISULFIDES BY CARBENES

CROSS-REFERENCE

This application is a 371 U.S. national phase of PCT/EP2021/060568, filed Apr. 22, 2021, which claims priority from EP 20170862.5, filed Apr. 22, 2020, both which are incorporated by reference in its entirety.

FIELD OF THE INVENTION

The present invention relates to a method for preparing a compound T having a thioether group from a compound D having a disulfide group in the presence of a carbene.

BACKGROUND OF THE INVENTION

Disulfide bonds are abundant in natural products, the tertiary structures of proteins and dynamic covalent libraries. Cleavage of the disulfide bond is most commonly initiated by the application of a nucleophilic reagent, such as thiolates and phosphines. The disulfide bond can be cleaved to a sulfenium cation in the presence of acids or a pair of thiyl radicals under UV irradiation. Furthermore, the irreversible preparation of a stable sulfide can also be achieved from disulfides, thus taking a dynamic starting material and fixing the linkage by the process of sulfur extrusion. The most common reagents for the extrusion process are aminophosphines, which have been widely applied and work for a broad scope of substrates. The synthesis of the lantibiotic Nisin for example was achieved by the utilization of tris(diethylamino)phosphine (cf. K. Fukase, M. Kitazawa, A. Sano, K. Shimbo, H. Fujita, S. Horimoto, T. Wakamiya, T. Shiba, *Tetrahedron Lett* 1988, 29, 795-798). Tris(diethylamino)phosphine was used to transform multiple disulfide bonds in the same molecule (cf. M. S. Collins, M. E. Carnes, B. P. Nell, L. N. Zakharov, D. W. Johnson, *Nat Commun* 2016, 7, 11052 and G. J. Bodwell, J. N. Bridson, S.-L. Chen, R. A. Poirier, *J Am Chem Soc* 2001, 123, 4704-4708), which until the above synthesis was typically achieved with the nucleophilic substitution of halides with sodium sulfide. Such an example is the conversion of dimeric and tetrameric disulfide cage compounds in quantitative yield to the corresponding sulfides (cf. Scheme 1).

The original preparation of the dimeric cage compound was reported by Boekelheide et al. (cf. V. Boekelheide, R. A. Hollins, *J Am Chem Soc* 1970, 92, 3512-3513) in a 12% yield using nucleophilic substitution (cf. Scheme 1 bottom). However, the same cage was later synthesized in 69% yield with additional 29% of the tetramer by Johnson et al. (cf. M. S. Collins, M. E. Carnes, B. P. Nell, L. N. Zakharov, D. W. Johnson, *Nat Commun* 2016, 7, 11052) via sulfur extrusion, highlighting the importance of dynamic covalent chemistry as an alternative to low yielding direct irreversible reactions. Importantly, this approach opens the possibility of post-functionalization around sulfur containing moieties.

Scheme 1: Synthesis of discrete cage molecules by sulfur extrusion (top) and nucleophilic substitution (bottom).

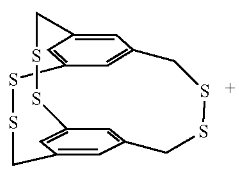

-continued

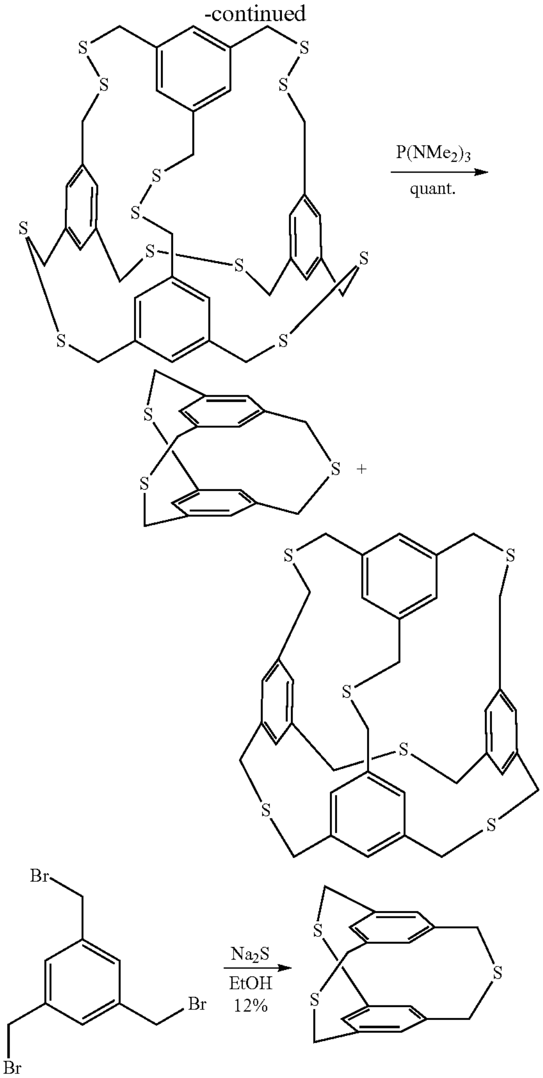

The extrusion of sulfur from a disulfide is a reaction which has been reported for the first time over 40 years ago and which has significant synthetic potential. Unfortunately, such extrusions are predominantly carried out by aminophosphine mediated protocols, most often using strong carcinogenic hexamethylphosphorus triamide in stoichiometric amounts. Since such compounds are avoided in industry and academia, the application of sulfur extrusion is rather limited until now despite its synthetic potential.

SUMMARY OF THE INVENTION

Thus, the technical problem underlying the present invention is to provide a novel sulfur extrusion method which avoids the use of the previously known unfavorable reagents, such as aminophosphines.

The solution to the above technical problem is achieved by the embodiments characterized in the claims.

In particular, the present invention relates to a method for preparing a compound T having a thioether group from a compound D having a disulfide group, wherein the method comprises the step of:

reacting the compound D in the presence of a carbene to form the compound T, wherein the compound D is a compound of the following general formula (1) and the compound T is a compound of the following general formula (3)

Formula (1)

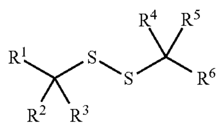

Formula (3)

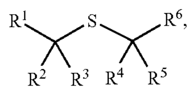

wherein $R^2$ to $R^5$ may be the same or different and are each independently selected from the group consisting of a hydrogen atom, a substituted or unsubstituted alkyl group, a substituted or unsubstituted alkenyl group, and a substituted or unsubstituted alkynyl group, wherein at least one of $R^2$ and $R^3$ is a hydrogen atom and at least one of $R^4$ and $R^5$ is a hydrogen atom; and $R^1$ and $R^6$ may be the same or different and are each independently selected from the group consisting of a substituted or unsubstituted aryl group, a substituted or unsubstituted heteroaryl group, a halogen atom, a group of the general formula (2), $—NZ^1Z^2$, $—NO_2$, —CN, $—OZ^3$, $—C(O)Z^4$, $—C(O)NZ^5Z^6$, $—COOZ^7$, and $—SO_3Z^8$, Formula (2)

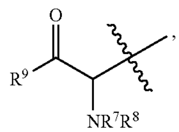

wherein $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, $—COOR^{10}$ and a peptide chain being bonded to the nitrogen atom of the $NR^7R^8$ group via its C terminus, wherein $R^{10}$ is selected from the group consisting of a substituted or unsubstituted alkyl group, a substituted or unsubstituted cycloalkyl group, a substituted or unsubstituted alkenyl group and a substituted or unsubstituted aryl group;

$R^9$ is selected from the group consisting of $—OR^{11}$ and a peptide chain being bonded to the carbon atom of the $C(O)R^9$ group via its N terminus, wherein $R^{11}$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

peptide chains, when present, may bond to each other via a peptide bond and/or via a disulfide bond and each of the peptide chains, when present, may have a disulfide bond within itself;

$Z^1$ to $Z^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; and $R^1$ to $R^6$ may bond to each other to form one or more rings; and wherein the carbene is a N-heterocyclic carbene.

DETAILED DESCRIPTION OF THE INVENTION

Figure 1:
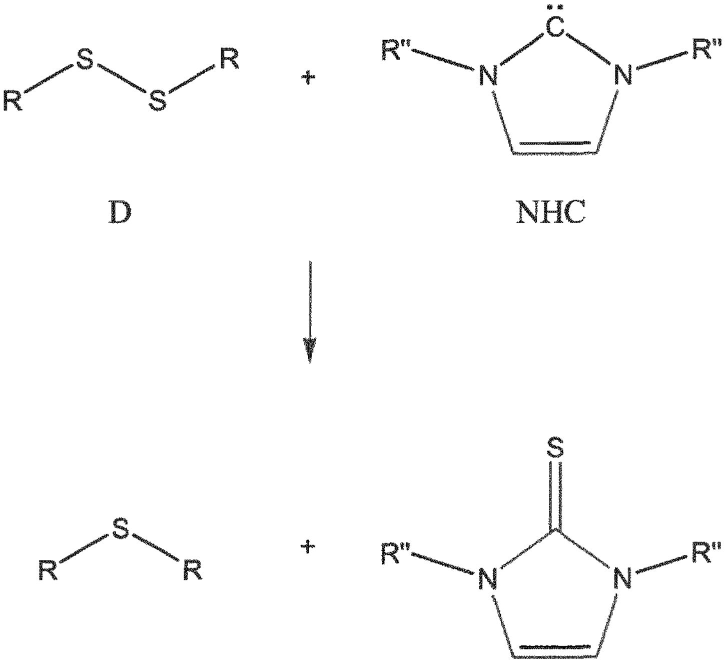
FIG. 1: Reaction of a compound D having a disulfide bond in the presence of an NHC giving the corresponding thioether T after sulfur extrusion and an NHC-thiourea derivative.

With the method of the present invention it is advantageously possible to form sulfides/thioethers from their corresponding disulfides via N-heterocyclic carbenes (NHCs) under mild conditions without the use of strong cancerogenic aminophosphines. Besides the obtained thioether, the respective thio derivative of the carbene, being a NHC thiourea compound, is produced (cf. FIG. 1). NHCs and the respective NHC thiourea compounds can be easily handled. Moreover, NHC thiourea compounds can be easily separated from the thioether. The respective thio derivative of the carbene, being a NHC thiourea compound, can be recycled using protocols known in the art (cf. for example T. Matsumura, M. Nakada, Tetrahedron Lett 2014, 55, 1412-1415 and D. M. Wolfe, P. R. Schreiner, Eur. J. Org. Chem. 2007, 2825-2838). Recycling is not necessarily carried out with the isolated thio derivatives of the carbenes, but can be carried out in situ. The carbenes can also be used in non-stochiometric amounts and recycled in situ, so that non-stochiometric amounts of carbene would be able to achieve the sulfur extrusion.

Herein, the term "thioether group" relates to a group with the connectivity C—S—C, wherein a sulfur atom is bonded to two organic residues. Accordingly, the term "disulfide group" relates to a group with the connectivity C—S—S—C, wherein two central sulfur atoms are bonded to two organic residues.

According to the present invention, the compound D has a disulfide group. The disulfide group of the compound D is converted to a thioether group by sulfur extrusion, thereby giving the compound T having a thioether group. The compound D is a compound of the following general formula (1)

Formula (1)

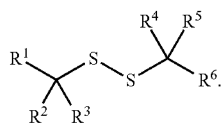

In the above general formula (1), $R^2$ to $R^5$ may be the same or different and are each independently selected from the group consisting of a hydrogen atom, a substituted or unsubstituted alkyl group, a substituted or unsubstituted alkenyl group, and a substituted or unsubstituted alkynyl group, wherein at least one of $R^2$ and $R^3$ is a hydrogen atom and at least one of $R^4$ and $R^5$ is a hydrogen atom. Preferably, $R^2$ to $R^5$ are each independently selected from a hydrogen atom and a substituted or unsubstituted alkyl group, wherein at least one of $R^2$ and $R^3$ is a hydrogen atom and at least one of $R^4$ and $R^5$ is a hydrogen atom. In case one of $R^2$ and $R^3$ is not a hydrogen atom and one of $R^4$ and $R^5$ is not a hydrogen atom, the respective non-hydrogen atom groups may bond to each other or each to $R^1$ and/or $R^6$ to form one or more rings, which may also have disulfide bonds. Most preferably, each of $R^2$ to $R^5$ is a hydrogen atom.

Moreover, in the above general formula (1), $R^1$ and $R^6$ may be the same or different and are each independently selected from the group consisting of a substituted or unsubstituted aryl group, a substituted or unsubstituted heteroaryl group, a halogen atom, a group of the general formula (2), $—NZ^1Z^2$, $—NO_2$, —CN, $—OZ^3$, $—C(O)Z^4$, $—C(O)NZ^5Z^6$, $—COOZ^7$, and $—SO_3Z^6$, Formula (2)

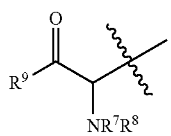

Preferably, $R^1$ and $R^6$ are each independently selected from the group consisting of a substituted or unsubstituted aryl group, a substituted or unsubstituted heteroaryl group, a group of the general formula (2), and $—COOZ^7$. Most preferably, $R^1$ and $R^6$ are each independently selected from a substituted or unsubstituted aryl group and a group of the general formula (2). $R^1$ and $R^6$ may bond to each other or each to any of $R^2$ to $R^6$, preferably to each other, to form one or more rings and/or $R^1$ and $R^6$ may be identical. In the case, where $R^1$ and $R^6$ may bond to each other or each to any of $R^2$ to $R^6$ to form one or more rings, e.g. cage structures, cyclophanes and peptides may be formed which have one or more disulfide bonds.

In the above general formula (2), $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group. More preferably, $R^7$ is selected from the group consisting of a hydrogen atom, a substituted or unsubstituted alkyl group, and a substituted or unsubstituted aryl group. Most preferably, $R^7$ is a hydrogen atom.

Moreover, in the above general formula (2), $R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, $—COOR^{10}$, and a peptide chain being bonded to the nitrogen atom of the $NR^7R^8$ group via its C terminus. Preferably, $R^8$ is selected from the group consisting of a hydrogen atom, a substituted or unsubstituted alkyl group, $—COOR^{10}$, and a peptide chain being bonded to the nitrogen atom of the $NR^7R^8$ group via its C terminus. Most preferably, $R^8$ is selected from $—COOR^{10}$ and a peptide chain being bonded to the nitrogen atom of the $NR^7R^6$ group via its C terminus. $R^{10}$ is selected from the group consisting of a substituted or unsubstituted alkyl group, a substituted or unsubstituted cycloalkyl group, a substituted or unsubstituted alkenyl group, and a substituted or unsubstituted aryl group. Preferably, $R^{10}$ is a substituted or unsubstituted alkyl group or a substituted or unsubstituted alkenyl group, most preferably a methyl group, a tert-butyl group, a benzyl group, a 9-fluorenylmethyl group, or an allyl group.

Furthermore, in the above general formula (2), $R^9$ is selected from the group consisting of $—OR^{11}$ and a peptide chain being bonded to the carbon atom of the $C(O)R^9$ group via its N terminus, wherein $R^{11}$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group. Preferably, $R^{11}$ is selected from a substituted or unsubstituted alkyl group and a substituted or unsubstituted aryl group, more preferably a substituted or unsubstituted alkyl group. Most preferably, $R^{11}$ is a methyl group.

The group of the above general formula (2) is derived from an amino acid. In case the group of the above general formula (2) is part of the compound D, further amino acids may be bonded to the C terminus and/or the N terminus of the group of the above general formula (2) giving a peptide. Such peptide chains may bond to each other or to parts of themselves via a (further) disulfide bond. Moreover, in case $R^1$ and $R^6$ both comprise peptide chains, said peptide chains may also bond to each other via a (further) disulfide bond and/or may bond to each other via a peptide bond (i.e. $R^1$ and $R^6$ bond to each other via the disulfide bond and/or the peptide bond between the peptide chains). Accordingly, multiple disulfide bonds may be present in the compound D, which may all be converted to thioether bonds via sulfur extrusion. In one embodiment, compound D is a polypeptide having one or more disulfide bonds, wherein the polypeptide is preferably selected from the group consisting of a disulfide precursor (i.e. before sulfur extrusion) of a lantibiotic, such as Nisin, Nisin A, Subtilin, Sublancin, and SapT.

In the above general formula (1), $Z^1$ to $Z^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group. Preferably, $Z^1$ to $Z^8$ are each independently selected from the group consisting of a hydrogen atom, a substituted or unsubstituted alkyl group, and a substituted or unsubstituted aryl group. Most preferably, $Z^1$ to $Z^8$ are each independently a substituted or unsubstituted alkyl group.

Moreover, the compound T is a compound of the following general formula (3)

Formula (3)

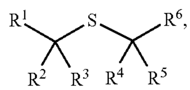

wherein $R^1$ to $R^6$ are defined as for the compound of the general formula (1).

If not stated otherwise, the following definitions apply to the terms "halogen", "alkyl group", "cycloalkyl group", "alkenyl group", "cycloalkenyl group", "alkynyl group", "aryl group", and "heteroaryl group". Herein the term "halogen" refers particularly to fluorine atoms, chlorine atoms, bromine atoms, and iodine atoms, preferably fluorine atoms and bromine atoms, most preferably fluorine atoms. The term "alkyl group" refers particularly to a branched or linear alkyl group having 1 to 20, preferably 1 to 12, more preferably 1 to 6, and most preferably 1 to 4 carbon atoms, which can be substituted or unsubstituted. Examples of alkyl groups represent methyl groups, ethyl groups, propyl groups, isopropyl groups, butyl groups, isobutyl groups, tert-butyl groups, pentyl groups, hexyl groups, and heptyl groups. The term "cycloalkyl group" refers particularly to a cycloalkyl group having 3 to 10, preferably 4 to 8, more preferably 5 or 6, and most preferably 6 carbon atoms, which can be substituted or unsubstituted. Examples of cycloalkyl groups represent cyclobutyl groups, cyclopentyl groups, and cyclohexyl groups. The term "alkenyl group" refers particularly to a branched or linear alkenyl group having 2 to 20, preferably 2 to 12, more preferably 2 to 6, and most preferably 2 to 4 carbon atoms, which can be substituted or unsubstituted. Examples of alkenyl groups represent vinyl groups and allyl groups. The term "cycloalkenyl group" refers particularly to a cycloalkenyl group having 4 to 10, preferably 5 to 8, more preferably 5 or 6, and most preferably 6 carbon atoms, which can be substituted or unsubstituted. Examples of cycloalkenyl groups represent cyclopentenyl groups, cyclopentadienyl groups, cyclohexyl groups, and cyclohexadienyl groups. The term "alkynyl group" refers particularly to a branched or linear alkynyl group having 2 to 20, preferably 2 to 12, more preferably 2 to 6, and most preferably 2 to 4 carbon atoms, which can be substituted or unsubstituted and which can be protected with e.g. TMS or TIPS groups. Examples of alkynyl groups represent ethynyl groups, 1-propynyl groups, and propargyl groups. The term "aryl group" refers particularly to an aryl group consisting of 1 to 6, preferably 1 to 4, more preferably 1 to 3 aromatic rings, and most preferably 1 ring, which can be substituted or unsubstituted. Examples of aryl groups represent phenyl groups, anthracenyl or naphthyl groups. The term "heteroaryl group" refers particularly to a heteroaryl group consisting of 1 to 6, preferably 1 to 4, more preferably 1 to 3 aromatic rings including heteroatoms, which can be substituted or unsubstituted. Heteroatoms, which are present in heteroaryl groups are for example N, O and S. Examples of heteroaryl groups represent pyridyl groups, pyrimidinyl groups, thienyl groups, furyl groups, or pyrrolyl groups.

According to the present invention, the alkyl groups, the cycloalkyl groups, the alkenyl groups, the cycloalkenyl groups, the alkynyl groups, the aryl groups, and the heteroaryl groups may be substituted or unsubstituted. The potential substituents are not specifically limited. Accordingly, instead of hydrogen atoms any substituent known in the prior art can be bonded to the further positions of the corresponding groups. For example, the potential substituents may be selected from the group consisting of a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms, a halogen atom, $—NL^1L^2$, $—NO_2$, —CN, $—OL^3$, $—C(O)L^4$, $—C(O)NL^5L^6$, $—COOL^7$, and $—SO_3L^8$, wherein $L^1$ to $L^8$ are each independently selected from a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms. Accordingly, examples of substituted alkyl groups are aralkyl groups or alkyl groups substituted with e.g. halogen atoms, such as e.g. a trifluoromethyl group, or any other of the above-mentioned substituents. The term "aralkyl group" refers particularly to an alkyl group wherein one or more hydrogen atoms, preferably terminal hydrogen atoms of the alkyl chain, are replaced by aryl or heteroaryl groups. Examples of aralkyl groups represent benzyl groups or 1- or 2-phenylethyl groups. Preferably, the potential substituents are selected from the group consisting of a branched or linear alkyl group having 1 to 6 carbon atoms, a branched or linear alkenyl group having 2 to 6 carbon atoms, a branched or linear alkynyl group having 2 to 6 carbon atoms, a halogen atom, $—NH_2$, $—NHCH_3$, $—N(CH_3)_2$, $—NO_2$, —OH, $—OCH_3$, —OEt, —C(O)H, $—C(O)CH_3$, —C(O)Et, and —COOH. Moreover, one or more tetravalent carbon atoms (together with the hydrogen atoms bonded thereto), when present, in each of the alkyl groups, the cycloalkyl groups, the alkenyl groups, the cycloalkenyl groups, and the alkynyl groups may each independently be substituted by a member selected from the group consisting of O, $(OCH_2CH_2)_nO$, S, $(SCH_2CH_2)_mS$, C(O), C(O)O, $NL^9$, and $C(O)NL^{10}$, preferably O, $(OCH_2CH_2)_nO$, C(O)O, and $C(O)NL^{10}$, wherein n and m are each independently an integer from 1 to 6. Accordingly, for example an alkyl group may be interrupted by e.g. one or more PEG linkers and/or amide bonds, and an alkenyl group may contain a C(O) group, such as in an acryloyl group. The way the groups are introduced instead of a carbon atom is not specifically limited. For example, a carbon atom may be substituted by C(O)O in the sense of —C(O)O— or —OC(O)— and by $C(O)NL^{10}$ in the sense of $—C(O)NL^{10}—$ or $—NL^{1Q}C(O)—$.

According to the present invention, $L^9$ and $L^{10}$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms, $—OG^1$, $—C(O)G^2$, $—C(O)NG^3G^4$, $—COOG^5$, and $—SO_2G^6$. In a preferred embodiment, $L^9$ and $L^{10}$ are each independently selected from the group consisting of a hydrogen atom, a branched or linear alkyl group having 1 to 6 carbon atoms, an aryl group having 1 to 3 aromatic rings, —C(O)$G^2$, and —$SO_2G^6$. Most preferably, $L^9$ and $L^{10}$ are each independently selected from the group consisting of a hydrogen atom and a branched or linear alkyl group having 1 to 6 carbon atoms. According to the present invention, $G^1$ to $G^6$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms. In a preferred embodiment, $G^1$ to $G^6$ are each independently selected from the group consisting of a hydrogen atom, a branched or linear alkyl group having 1 to 6 carbon atoms, an aryl group having 1 to 3 aromatic rings.

If not stated otherwise, the alkyl groups, the cycloalkyl groups, the alkenyl groups, the cycloalkenyl groups, the alkynyl groups, the aryl groups, and the heteroaryl groups are preferably unsubstituted. Moreover, if not stated otherwise, the alkyl groups, the alkenyl groups, and the alkynyl groups are preferably linear.

According to the present invention, compound D has at least one disulfide bond. Accordingly, compound D may have more than one disulfide bond, e.g. from 1 to 20 disulfide groups, which can be converted partially or fully to the corresponding thioether bonds by the method of the present invention. Preferably, the disulfide bonds possess similar substitution patterns as defined with respect to the above-mentioned Formula (1), in particular similar groups $R^1$ and $R^6$ attached to carbon atoms bonded to the disulfide bond. For example, in the method according to present invention, from 25% to 100% of (the total of) the disulfide groups of compound D can be converted into thioether groups in the compound T. Preferably, from 50% to 100%, more preferably from 70% to 100%, more preferably 80 to 100%, more preferably 90 to 100%, most preferably 100% of (the total of) the disulfide groups of compound D can be converted into thioether groups in the compound T.

As outlined above, $R^1$ and $R^6$ and $R^2$ to $R^5$ may bond to each other to form one or more rings. Examples of corresponding compounds D are peptides wherein peptide chains present in $R^1$ and $R^6$ bond to each other via a peptide bond and/or further disulfide bonds, such as in the case of precursor compounds of lantibiotics, such as Nisin. Further examples are other compounds having oligomeric, polymeric, macrocyclic, or cage structures and having one or more disulfide bonds, such as cyclophanes and oligo- and/or polysaccharides having one or more disulfide bonds. After sulfur extrusion the disulfide bonds(s) present in compound D are converted entirely or at least partially to the respective thioethers. With respect to the above Examples, peptides, such as lantibiotics, as e.g. Nisin, and compounds having oligomeric, polymeric, macrocyclic, or cage structures, such as cyclophanes and oligo- and/or polysaccharides, which have one or more thioether bonds in the corresponding compound T are obtained.

Exemplary structures for cyclophanes are given by the following formulae (4) and (5), wherein formula (4) represents a respective compound D and formula (5) represents a respective compound T, wherein M represents the groups linking the different disulfide/thioether groups and p is an integer from 0 to 6. The groups M are derived from the groups $R^1$ and $R^6$ and/or the groups $R^2$ to $R^5$.

Formula (4)

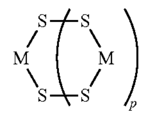

Formula (5)

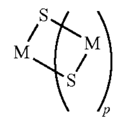

According to the present invention, the method for preparing a compound T having a thioether group from a compound D having a disulfide group comprises the step of: reacting the compound D in the presence of a carbene, being a N-heterocyclic carbene, to form the compound T. The carbene may be added in an amount of at least 1.0 equivalents in relation to the amount of disulfide groups in compound D or may be added in catalytic amounts, such as in an amount of 0.01 to 0.2 equivalents in relation to the amount of disulfide groups in compound D. When added in catalytic amounts, there can be added reagents, which are able to regenerate the reacted carbene. These reagents are then added in amounts so that the amount of carbene available for converting the compound D having a disulfide group to the compound T having a thioether group is at least 1.0 equivalents, more preferably at least 1.1 equivalents, more preferably at least 1.2 equivalents, and even more preferably at least 1.3 equivalents in relation to the amount of disulfide groups in compound D. For example, for regeneration of NHC compounds from NHC thiourea compounds, there may be used a Pd-catalyzed method for the preparation of the corresponding imidazolinium salts with triethylsilane and trialkylsilyl triflate (cf. T. Matsumura, M. Nakada, Tetrahedron Letters 55 (2014), pp. 1412-1415). Preferably, the carbene is present in an amount of at least 0.1 equivalents in relation to the amount of disulfide groups in compound D. More preferably, the carbene is present in an amount of at least 0.2 equivalents, more preferably at least 0.3 equivalents, more preferably at least 1.0 equivalents, more preferably at least 1.1 equivalents, more preferably at least 1.2 equivalents, and even more preferably at least 1.3 equivalents in relation to the amount of disulfide groups in compound D. The upper limit of the amount of carbene is preferably 2.5 equivalents in relation to the amount of disulfide groups in compound D, more preferably 2.0 equivalents in relation to the amount of disulfide groups in compound D. Most preferably, the carbene is present in an amount of 1.5 equivalents in relation to the amount of disulfide groups in compound D.

The further reaction conditions are not particularly limited. For example, the compound D may be reacted in the presence of a solvent or the carbene and the compound D may be mixed as such, e.g. by using a ball mill or ionic liquids having carbene subunits, such as 1-Butyl-3-methylimidazolium hexafluorophosphate (BMIM-$PF_6$). Preferably, the compound D is reacted in the presence of the carbene and in the presence of a solvent. The applied solvent is not particularly limited. For example, the solvent may be any suitable polar or non-polar solvent, such as one or more selected from the group consisting of 1,4-dioxane, diethyl ether, water, ionic liquids, halogenated solvents, DMSO, THF, DMF, acetonitrile, toluene, n-hexane, methanol, ethanol, and isopropanol.

The amount of solvent used with respect to the compound D is not particularly limited. For example, the (total) amount of solvent may be from 1.0 L to 1000 L per 1.0 mole of compound D. The (total) amount of solvent is preferably from 10 L to 100 L, more preferably from 20 L to 80 L, most preferably from 30 L to 50 L per 1.0 mole of compound D.

Moreover, the temperature at which the step of reacting the compound D is carried out is not particularly limited. For example, the temperature may be at least 0° C., preferably at least 20° C., and more preferably at least 40° C. The upper limit of the temperature is not particularly limited but may dependent on the reactants and potential solvents used. For example, the upper limit of the temperature may be 80° C., preferably 70° C., and more preferably 60° C. Most preferably, the temperature at which the step of reacting the compound D is carried out is 50° C.

Furthermore, the duration for which the step of reacting the compound D is carried out is not particularly limited. For example, the duration may be from 30 s to 10 d, preferably from 5 min to 6 d, more preferably from 2 h to 4 d, and more preferably from 8 h to 2 d.

The carbene, i.e. the N-heterocyclic carbene, can either be applied as free carbene or can be obtained from the corresponding protonated salt and a base. Preferably, the carbene is obtained from the corresponding protonated salt and a base, since the protonated salts are often commercially available, easily handled and air stable. The base used for generating the carbene from the protonated salt is not particularly limited. For example, the base may be selected from the group consisting of a hydride, such as NaH, a carbonate, such as $K_2CO_3$ and $Cs_2CO_3$, an alcoholate, such as KOtBu, DBU, alkali HMDS, such as LiHMDS, NaHMDS, and KHMDS, and LDA. The base is preferably selected from a hydride and a carbonate, more preferably selected from NaH and $K_2CO_3$. Most preferably, $K_2CO_3$ is used as the base. The amount of base used with respect to the amount of protonated carbene salt (in terms of mole) may be from 1.0 to 5.0 equivalents (in terms of mole), preferably from 2.0 to 4.0 equivalents. Most preferably, 3.0 equivalents of base are used with respect to the amount of protonated carbene salt. Preferably, the carbene is first provided/generated before adding compound D.

The N-heterocyclic carbene which is used in the present invention is not particularly limited. For example, the N-heterocyclic carbene may be an imidazolylidene, a thiazolylidene, an oxazolylidene, an imidazolidinylidene, a 1,2,4-triazolylidene, a 1,2,3-triazolylidene, a benzimidazolylidene, a pyrrolylidene, a tetrahydropyrimidinylidene, a triazinylidene, a diazepanylidene, an imidazo[1,2-a]pyridinylidene, an imidazo[1,5-a]pyridinylidene, a diazocanylidene, a N,N-dialkylamidocarbene, a cyclic (alkyl)(amino)carbene, an imidazo[5,1-b]thiazolylidene, a triazadiborinylidene, a [1,2,4]triazolo[4,3-a]pyridin-3-ylidene, an indazolylidene, and an isoquinolin-1-ylidene. Preferably, the carbene is selected from the group consisting of 1,3-bis(2,4,6-trimethylphenyl)-1,3-dihydro-2H-imidazol-2-ylidene, 1,3-bis(2,4,6-trimethylphenyl)imidazol-2-ylidene (IMes), 1,3-bis(2,6-diisopropylphenyl)imidazol-2-ylidene (IPr), 1,3-bis(2,4,6-trimethylphenyl)-4,5-dihydroimidazol-2-ylidene (SIMes), 1,3-diisopropylimidazol-2-ylidene (NHC-4), 1,3-dimethylbenzimidazol-2-ylidene (NHC-5), and 1,4-dimethyl-4H-1,2,4-triazol-5-ylidene (NHC-6). The N-heterocyclic carbene is preferably selected from IMes, IPr, SIMes, and NHC-4, more preferably from IMes, SIMes, NHC-4. Most preferably, the N-heterocyclic carbene is IMes.

The step of reacting the compound D may be carried out in the presence of air, in particular in case a protonated carbene salt is used, or in the presence of an inert and/or dry atmosphere. Preferably, the step of reacting the compound D is carried out in the presence of an inert and/or dry atmosphere, in particular in case a free carbene is used. For example, the step of reacting the compound D can be carried out under nitrogen atmosphere or argon atmosphere, preferably under argon atmosphere.

The compound D may be added as such (e.g. prepared and isolated in previous steps or obtained commercially) or may be prepared in situ. For example, the compound D may be prepared in situ from the respective thiol compounds, e.g. by further adding oxidizing reagents, and then further converted to the compound T.

In potential subsequent steps, the thioether compound T may be purified and isolated by various methods known in the art. For example, the converted carbene, e.g. generated NHC-thiourea compound, and/or unreacted starting material and/or potential side-products may be removed by filtration, distillation, alkaline extraction, subsequent reactions or column chromatography from the reaction mixture. As a subsequent reaction, disulfides may for example be reduced to thiols by reducing agents, such as $NaBH_4$ and phosphines.

The isolated yield of the compound T is not particularly limited. For example, the isolated yield of the compound T in relation to the amount of compound D may be at least 25%. Preferably, the isolated yield of the compound T in relation to the amount of compound D is at least 30%, more preferably at least 35%, more preferably at least 40%, more preferably at least 50%, more preferably at least 60%, more preferably at least 70%, and most preferably at least 80%.

The present invention will be further illustrated in the following examples without being limited thereto.

EXPERIMENTAL PROCEDURES

General

All reagents and solvents were used without further purification unless otherwise noted. For thin layer chromatography silica gel 60 F254 plates from Merck were used and examined under UV-light irradiation (254 nm and 365 nm). Flash column chromatography was performed on silica gel from Sigma-Aldrich (particle size: 0.04-0.063 mm) using petroleum ether, dichloromethane, toluene and/or ethyl acetate. Recycling high performance liquid chromatography was performed with a Shimadzu LC-20AP preparative pump unit, CBM-20A communication bus module, SPD-M20A diode array detector, FCV-20AH2 valve unit and a Restek ultra silica 5 μm (250×21.2 mm) normal phase column or Macherey-Nagel nucleodur 100-5 C18ec reverse phase column. Melting points (not corrected) were measured with a Büchi Melting Point B-545. IR-Spectra were recorded on a Bruker Tensor 27 spectrometer on a ZnSe ATR crystal. NMR spectra were taken on a Bruker DRX 300 (300 MHz), Bruker Avance 300 μl (300 MHz), Bruker Avance III 400 (400 MHz), Bruker Avance III 500 (500 MHz) and Bruker Avance III 600 (600 MHz) spectrometer. Chemical shifts (δ) are reported in parts per million (ppm) relative to traces of the nondeuterated solvent in the corresponding deuterated solvent. Electron Impact Ionization experiments (EI) were carried out on a JEOL AccuTOF GCx spectrometer. Electrospray ionization (ESI) mass spectra were recorded on a Finnigan LCQ quadrupole ion trap. Molecule fragments were given as a mass-to-charge proportion (m/z). Elemental analysis was performed by the Microanalytical Laboratory of the University of Heidelberg using an Elementar Vario EL machine.

General Procedure for Sulfur Extrusion Screening Experiments

Under an argon atmosphere 1,2-bis(4-methylbenzyl)disulfide (20.0 mg, 72.9 μmol, 1.0 eq) and NHC salt (1.0 eq) were suspended in dry solvent (3 mL). Base (219 μmol, 3.0 eq) was added. The reaction was stirred for 24 h at 50° C. Afterwards the solvent was removed under reduced pressure and the residue was suspended and ultrasonicated for 3 min in a prepared 8.92 mM solution of 1,3,5-trimethoxy benzene (TMB) in $CDCl_3$ (2 mL). After the NMR measurement the NMR yield was determined in comparison of the integrals of TMB $OCH_3$ (3.77 ppm) and sulfide $CH_2$ (3.56 ppm).

Figure 2:
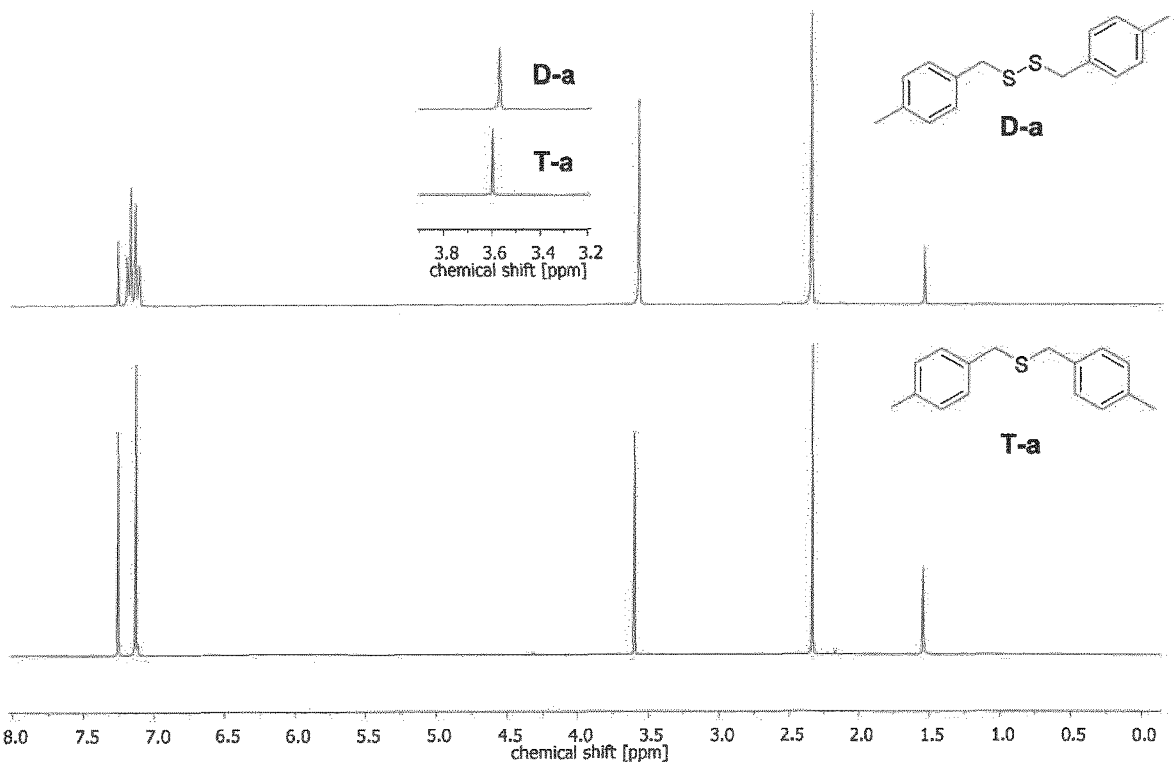
FIG. 2: Comparison of $^1H$ NMR (300 MHz, $CDCl_3$) of model disulfide (top) and model sulfide (bottom).

In FIG. 2 there is shown a comparison of $^1H$ NMR (300 MHz, $CDCl_3$) spectra of a model disulfide and a model sulfide.

Synthesis of bis(4-methylbenzyl)sulfide

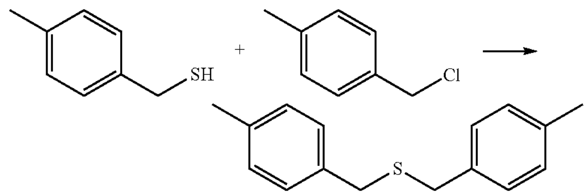

Potassium hydroxide (0.84 g, 15.0 mmol, 2.0 eq) was suspended in ethanol (10 mL). 4-Tolylmethanethiol (1.00 mL, 7.49 mmol, 1.0 eq) and 4-methylbenzylchloride (1.05 g, 991 μmol, 1.0 eq) were added. The reaction was stirred at rt overnight. The precipitate was filtered off and washed with ethanol (50 mL) and water (100 mL). The product was obtained as a colourless solid (1.15 g, 64%). The analytical data are consistent with those from literature (cf. K. S. Eccles, C. J. Elcoate, S. E. Lawrence, A. R. Maguire, *Gen. Pap. Ark.* 2010, ix, 216-228).

Melting point: 78° C. (Lit.: 76-78° C.). $^1H$-NMR (300 MHz, $CDCl_3$): δ (ppm)=7.18-7.17 (m, 4H, Ar—H), 7.13-7.11 (m, 4H, Ar—H), 3.57 (s, 4H, Ar—$CH_2$—S), 2.34 (s, 6H, Ar—$CH_3$).

Preparation of Disulfide Compounds

General Procedures for the Preparation of Disulfide Compounds

General Procedure for Synthesis of Thiols (GP1)

Halogenide (10.0 mmol, 1.0 eq) was dissolved in ethanol (5 mL). Thiourea (800 mg, 10.5 mmol, 1.05 eq) was added and the solution was stirred under reflux overnight. The mixture was allowed to obtain rt and the solvent was removed under reduced pressure. The residue was dissolved in 2.5 M sodium hydroxide solution (20 mL) and refluxed for 2 h at 85° C. The mixture was allowed to obtain rt and was acidified to pH 1-2 with sulfuric acid (15% (v/v), 5 mL). The mixture was extracted with dichloromethane (2×20 mL) and the combined organic layer were dried over anhydrous sodium sulfate. The solvent was removed under reduced pressure to obtain the product. The product was used for the synthesis of the corresponding disulfide without further purification or characterization.

General Procedure for Synthesis of Disulfides (GP2)

The synthesis of disulfides was performed according to a literature known procedure (cf. B. Zeynizadeh, *J. Chem. Res.* 2002, 2002, 564-566). Thiol (10.0 mmol, 1.0 eq) was dissolved in a 5:1 mixture of acetonitrile (20 mL) and water (5 mL). Afterwards iodine (1.27 g, 5.00 mmol, 0.5 eq) was added and the reaction was stirred at rt for 15 min. After TLC indicated full completion, a saturated solution of sodium sulfite in water (30 mL) was added to the reaction. The mixture was extracted with dichloromethane (2×50 mL) and the combined organic layers were dried over anhydrous sodium sulfate. The solvents were removed under reduced pressure to obtain the disulfide.

Synthesis of 1,2-bis(4-methylbenzyl)disulfide D-a

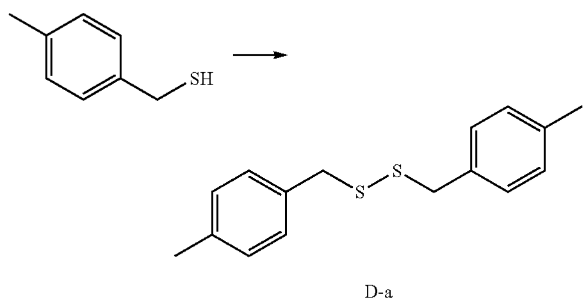

D-a

Disulfide D-a was synthesized according to GP2 from 4-methylbenzylmercaptane (1.05 mL, 1.09 g, 7.86 mmol, 1.0 eq) and obtained as a colourless solid (1.05 g, 3.83 mmol, quant.). The analytical data are consistent with those from literature (cf. B. Zeynizadeh, *J. Chem. Res.* 2002, 2002, 564-566).

Melting point: 46° C. (Lit.: 46° C.). $^1H$ NMR (600 MHz, $CDCl_3$): δ (ppm)=7.12 (m, 8H, Ar—H), 3.61 (s, 4H, Ar—$CH_2$—S), 2.32 (s, 6H, Ar—$CH_3$).

Synthesis of 1,2-bis(4-methoxybenzyl)disulfide D-b

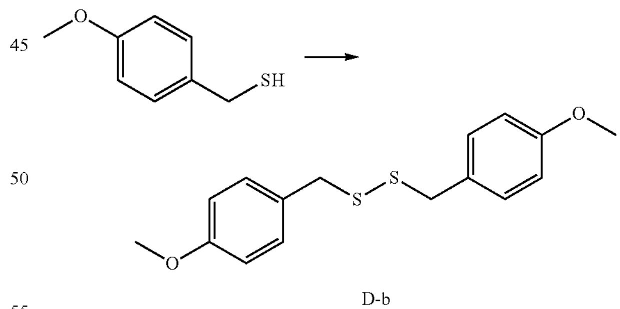

D-b

Disulfide D-b was synthesized according to a literature known procedure (cf. U. F. Fritze, M. von Delius, *Chem. Commun.* 2016, 52, 6363-6366). The product was obtained as a colourless solid (2.48 g, 8.10 mmol, quant.). The analytical data are consistent with the above literature.

Melting point: 94° C. (Lit. (cf. H. Xiao, J. Chen, M. Liu, H. Wu, J. Ding, Phosphorus, Sulfur Silicon Relat. Elem. 2009, 184, 2553-2559): 99° C.). $^1H$ NMR (300 MHz, $CDCl_3$): δ (ppm)=7.17 (m, 4H, Ar—H), 6.86 (m, 4H, Ar—H), 3.80 (s, 6H, Ar—$CH_2$—S), 3.59 (s, 4H, $OCH_3$).

Synthesis of 1,2-bis(4-bromobenzyl)disulfide D-c

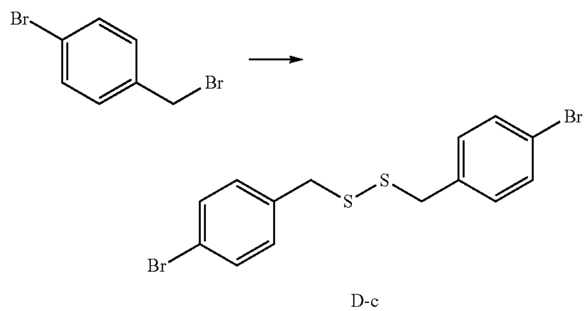

D-c

Disulfide D-c was synthesized according to GP1 followed by GP2 from 4-bromobenzylbromide (5.00 g, 11.4 mmol, 1.0 eq). The product was obtained as a colourless solid (4.61 g, 4.37 mmol, 93%, over two steps). The analytical data are consistent with those from literature (cf. K. M. Khan, M. Taha, F. Rahim, M. Ali, W. Jamil, S. Perveen, M. Iqbal Choudhary, *Lett. Org. Chem.* 2010, 7, 415-419).

Melting point: 80° C. (Lit.: 83-84° C.). $^1H$ NMR (300 MHz, $CDCl_3$): δ (ppm)=7.44 (d, J=8.4 Hz, 4H, Ar—H), 7.43 (d, J=8.4 Hz, 4H, Ar—H), 3.62 (s, 4H, Ar—$CH_2$—S).

Synthesis of 1,2-bis(4-methylbenzoate)disulfide D-d

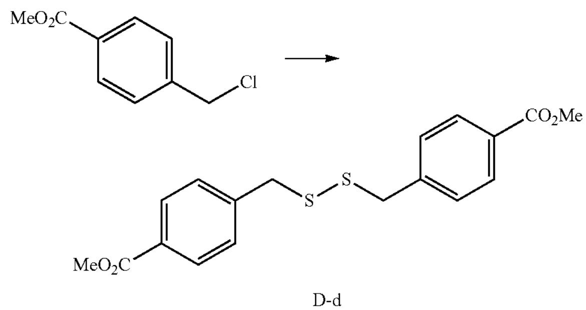

D-d

Disulfide D-d was synthesized according to a procedure for direct conversation of benzylic halogenides to disulfides (cf. D. Preeti, S. Chandrasekaran, *J. Org. Chem* 1989, 54, 2998-3000). Methyl-4-(chloromethyl)benzoate (1.85 g, 10.0 mmol, 1.0 eq) was dissolved in DMF (20 mL) and added dropwise to a solution of ammonium tetrathiomolybdate (2.60 g, 10.0 mmol, 1.0 eq) in DMF (30 mL) at rt. The mixture was stirred overnight. Water (50 mL) was added and the solution was extracted with methyl tert-butyl ether (2×50 mL). The combined organic phases were extracted with water (3×40 mL) until the aqueous phase was colourless. The organic phase was dried over anhydrous sodium sulfate and the solvent was removed under reduced pressure. The crude product was further purified by column chromatography ($SiO_2$, PE:DCM 1:1) to obtain the pure product as a colourless solid (1.16 g, 3.20 mmol, 64%).

Melting point: 79° C. $^1H$ NMR (400 MHz, $CDCl_3$): δ (ppm)=7.99 (d, J=8.20 Hz, 4H, Ar-3-H), 7.28 (d, J=8.20 Hz, 4H, Ar-2-H), 3.91 (s, 6H, $CO_2CH_3$), 3.61 (s, 4H, Ar—$CH_2$—S). $^{13}C$ NMR (100 MHz, $CDCl_3$): δ (ppm) =166.9 (Ar—$CO_2$Me), 142.7 (Ar—C-1), 129.9 (Ar—C-3), 129.5 (Ar—C-2), 129.4 (Ar—C-4), 52.3 ($CO_2CH_3$), 43.0 (Ar—$CH_2$—S). FT-IR (ATR): ṽ ($cm^{-1}$)=3063 (vw), 3028 (w), 2999 (w), 2951 (w), 2914 (w), 2842 (w), 2081 (vw), 1989 (vw), 1964 (vw), 1907 (vw), 1718 (vs), 1606 (w), 1588 (w), 1485 (w), 1445 (m), 1433 (m), 1305 (m), 1283 (vs), 1223 (m), 1199 (s), 1104 (s), 1079 (m), 988 (m), 916 (w), 872 (w), 857 (vw), 818 (w), 794 (m), 758 (s), 717 (m), 699 (s), 673 (m), 660 (w). HRMS (El, pos): m/z calcd. for [$M^+$]: 362.0647, found: 362.0641 (<10), 149.0598 (100), 121.0662 (14), 90.0466 (11). Elemental analysis: Calcd. for $C_{18}H_{18}O_4S_2$: C, 59.65, H, 5.01; found: C, 59.67, H, 5.15.

Synthesis of 1,2-bis(4-trifluoromethylbenzyl)disulfide D-e

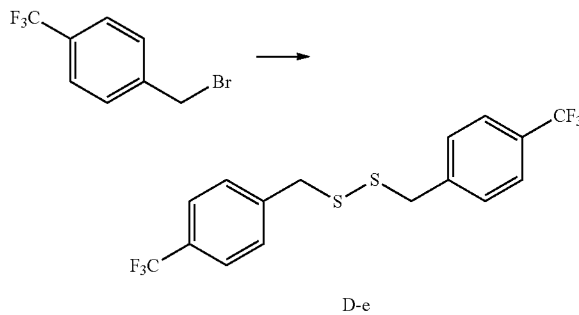

D-e

Disulfide D-e was synthesized according to GP1 followed by GP2 from 4-trifluoromethylbenzylbromide (2.39 g, 10.0 mmol, 1.0 eq). The product was obtained as a colourless solid (1.67 g, 4.37 mmol, 87%, over two steps). The analytical data are consistent with those from literature (cf. S. L. Buchwald, R. B. Nielsen, *J. Am. Chem. Soc* 1988, 110, 3171-3175; R. Matake, Y. Niwa, H. Matsubara, *Tetrahedron Lett.* 2016, 57, 672-675).

Melting point: 67° C. (Lit.: 65-68° C.). $^1H$ NMR (300 MHz, $CDCl_3$): δ (ppm)=7.59 (d, J=8.1 Hz, 4H, Ar—H), 7.32 (d, J=8.1 Hz, 4H, Ar—H), 3.65 (s, 4H, Ar—$CH_2$—S).

Synthesis of 1,2-bis(3-methoxybenzyl)disulfide D-f

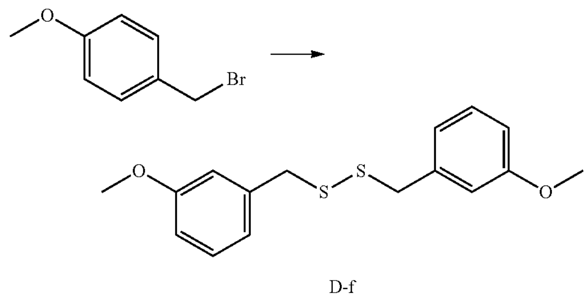

D-f

Disulfide D-f was synthesized according to GP1 followed by GP2 from 3-methoxybenzylbromide (1.66 mL, 2.39 g, 11.9 mmol, 1.0 eq). The product was obtained as a colourless oil (1.37 g, 4.48 mmol, 77%, over two steps). The analytical data are consistent with those from literature (cf. V. Panduranga, G. Prabhu, N. Panguluri, B. Nageswara, R. Panguluri, V. V. Sureshbabu, *Synthesis* (*Stuttg*). 2016, 48, 1711-1718).

$^1$H-NMR (300 MHz, $CDCl_3$): δ (ppm)=7.23 (m, 2H, Ar—H), 6.83 (m, 6H, Ar—H), 3.81 (s, 6H, Ar—$CH_2$—S), 3.61 (s, 4H, $OCH_3$).

Synthesis of 1,2-bis(3-methylbenzoate)disulfide D-g

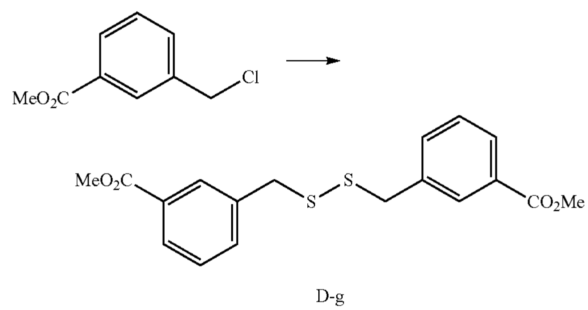

D-g

Disulfide D-g was synthesized as D-d. The product was obtained as a sticky colourless oil (872 mg, 2.40 mmol, 48%).

$^1$H NMR (400 MHz, $CDCl_3$): δ (ppm)=7.97-7.94 (m, 2H, Ar-5-H), 7.90 (m, 2H, Ar-2-H), 7.42-7.40 (m, 4H, Ar-4/6-H), 3.93 (s, 6H, $CO_2CH_3$), 3.64 (s, 4H, Ar—$CH_2$—S). $^{13}$C NMR (100 MHz, $CDCl_3$): δ (ppm)=166.9 (Ar—$CO_2$Me), 137.9 (Ar—C-2), 134.0 (Ar—C-4), 130.7 (Ar—C-3), 130.6 (Ar—C-2), 128.9 (Ar—C-5), 128.8 (Ar—C-6), 52.3 (Ar—$CO_2CH_3$), 42.9 (Ar—$CH_2$—S). FT-IR (ATR): ṽ ($cm^{-1}$) =3061 (vw), 3026 (w), 2999 (w), 2951 (w), 2913 (w), 2842 (w), 2080 (vw), 1988 (vw), 1965 (vw), 1905 (vw), 1717 (vs), 1606 (w), 1589 (w), 1485 (w), 1445 (m), 1433 (m), 1305 (m), 1283 (vs), 1223 (s), 1199 (s), 1104 (s), 1079 (m), 988 (m), 916 (w), 872 (w), 819 (w), 794 (m), 757 (s), 717 (m), 699 (s), 674 (m), 660 (w). HRMS (El, pos): m/z calcd. for [$M^+$]: 362.0647, found: 362.0645 (<10), 149.0597 (100), 119.0499 (11). Elemental analysis: Calcd. for $C_{18}H_{18}O_4S_2$: C, 59.65, H, 5.01; found: C, 59.88, H, 5.19.

Synthesis of 1,2-bis(3-trifluoromethylbenzyl)disulfide D-h

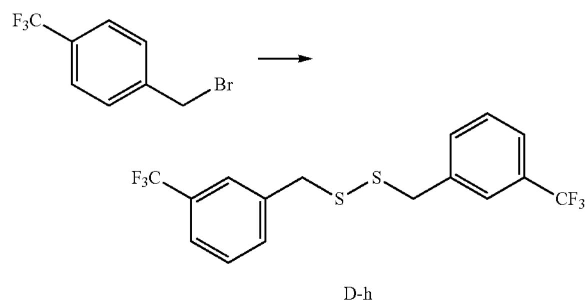

D-h

Disulfide D-h was synthesized according to GP1 followed by GP2 from 3-trifluoromethylbenzylbromide (1.53 mL, 2.39 g, 10.0 mmol, 1.0 eq). The product was obtained as a colourless oil (2.21 g, 5.79 mmol, quant., over two steps). The analytical data are consistent with those from literature (cf. H. Huang, J. Ash, J. Y. Kang, *Org. Biomol. Chem.* 2018, 16, 4236).

$^1$H NMR (300 MHz, $CDCl_3$): δ (ppm)=7.55 (m, 2H, Ar—H), 7.43 (m, 6H, Ar—H), 3.62 (s, 4H, Ar—$CH_2$—S).

Synthesis of 1,2-bis((perfluorophenyl)methyl)disulfide D-i

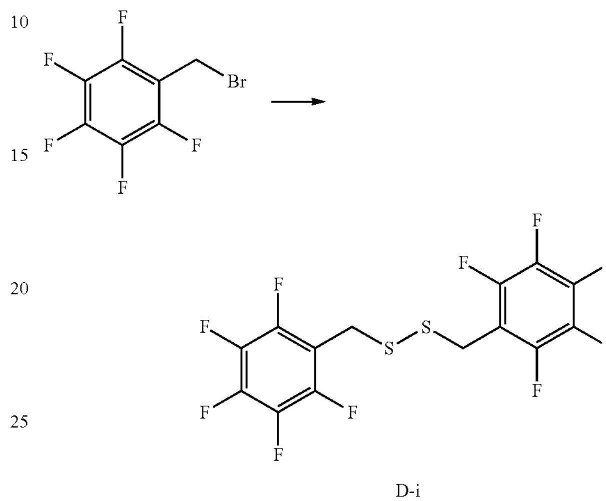

D-i

Disulfide D-i was synthesized by addition of perfluorophenylmethyl bromide (2.61 g, 10.0 mmol, 1.0 eq) to a solution of potassium thioacetate (1.37 g, 10.5 mmol, 1.2 eq) in tetrahydrofuran (30 mL). The reaction was stirred at rt overnight. The solvent was removed under reduced pressure and the residue was dissolved in methanol (5 mL). Trifluoroacetic acid (5 mL) was added and the reaction was stirred under reflux for 3 days. The mixture was diluted with water (200 mL) and aqueous sodium hydroxide solution (20 wt %, 40 mL) was added. The aqueous mixture was extracted with dichloromethane (3×50 mL). The combined organic phases were dried over anhydrous sodium sulfate and the solvent was removed under reduced pressure. The product was obtained as a colourless solid (700 mg, 1.70 mmol, 34%, over two steps). The analytical data are consistent with those from literature (cf. C. H. Sohn, C. K. Chung, S. Yin, P. Ramachandran, J. A. Loo, J. L. Beauchamp, *J. Am. Chem. Soc* 2009, 131, 5444-5459).

Melting point: 135-138° C. (Lit. (cf. G. M. Brooke, J. A. K. J. Ferguson, J. Fluor. Chem. 1988, 41, 263-275): 145.5° C.). $^1$H NMR (300 MHz, $CDCl_3$): δ (ppm)=3.91 (s, 4H, Ar—$CH_2$—S).

Synthesis of 1,2-bis(2,4,6-trimethylbenzyl)disulfide D-j

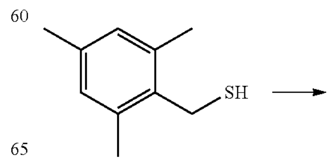

-continued

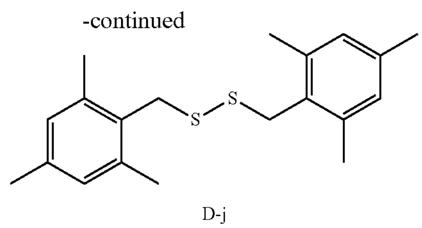

D-j

Disulfide D-j was synthesized according to GP2 from 2,4,6-trimethylbenzylmercaptane (5.00 g, 30.1 mmol, 1.0 eq) and obtained as a colourless solid (4.77 g, 14.6 mmol, 97%).

Melting point: 96° C. $^1H$ NMR (400 MHz, $CDCl_3$): δ (ppm)=6.83 (s, 4H, Ar-3/5-H), 3.92 (s, 4H, Ar—$CH_2$—S), 2.36 (s, 12H, Ar-2/6-$CH_3$), 2.24 (s, 6H, Ar-4-$CH_3$). $^{13}C$ NMR (100 MHz, $CDCl_3$): δ (ppm)=137.5 (Ar—C-1), 137.2 (Ar—C-4), 130.1 (Ar—C-2/6), 129.3 (Ar—C-3/5), 38.7 (Ar—$CH_2$—S), 21.1 (Ar-6-$CH_3$), 20.0 (Ar-2/5-$CH_3$). FT-IR (ATR): ṽ ($cm^{-1}$)=3000 (w), 2966 (w), 2949 (w), 2910 (w), 2862 (w), 2724 (vw), 2670 (vw), 2395 (vw), 2326 (vw), 2253 (vw), 2186 (vw), 2152 (vw), 2141 (vw), 2056 (vw), 1990 (vw), 1951 (vw), 1913 (vw), 1886 (vw), 1765 (vw), 1726 (vw), 1691 (w), 1640 (vw), 1610 (m), 1577 (w), 1534 (w), 1481 (m), 1459 (m), 1440 (m), 1421 (m), 1373 (m), 1222 (w), 1195 (w), 1140 (w), 1120 (w), 1029 (m), 1015 (w), 943 (vw), 851 (vs), 768 (w), 742 (w), 679 (m), 643 (w). HRMS (El, pos): m/z calcd. for [$M^+$]: 330.1476, found: 330.1470 (<1), 133.1009 (100). Elemental analysis: Calcd. for $C_{20}H_{26}S$: C, 72.67, H, 7.93; found: C, 72.41, H, 8.19.

Synthesis of dimethyl 2,2'-disulfidediyldiacetate D-l

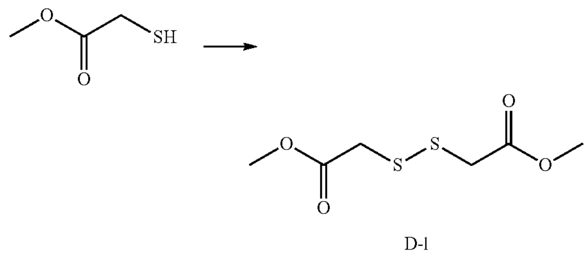

D-l

Disulfide D-1 was synthesized according to GP2 from methylthioglyconate (1.06 g, 10.0 mmol, 1.0 eq). The product was obtained as a colourless oil (1.05 g, 5.00 mmol, quant.). The analytical data are consistent with those from literature (cf. S. S. Shah, S. Karthik, N. D. P. Singh, *RSC Adv.* 2015, 5, 45416-45419).

$^1H$ NMR (300 MHz, $CDCl_3$): d (ppm)=3.77 (s, 6H, $CO_2CH_3$) 3.59 (s, 4H, $CH_2$—S).

Synthesis of dimethyl 3,3'-disulfidediyl(2R,2'R)-bis (2-((tert-butoxycarbonyl) amino)propanoate) D-m

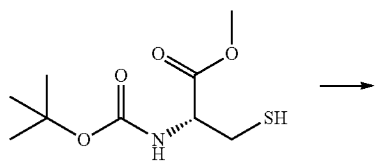

-continued

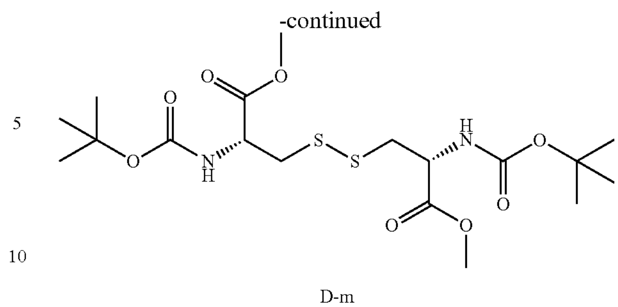

D-m

Disulfide D-m was synthesized according to a literature known procedure (cf. P. Mampuys, Y. Zhu, S. Sergeyev, E. Ruijter, R. V. A. Orru, S. Van Doorslaer, B. U. W. Maes, *Org. Lett.* 2016, 18, 2808-2811). The product was obtained as a colourless oil which solidified after several days at room temperature to a colourless solid (1.74 g, 3.70 mmol, 74%). The analytical data are consistent with the above from literature.

Melting point: 92° C. (Lit.: 99-100° C.). $^1H$ NMR (300 MHz, $CDCl_3$): δ (ppm)=5.36 (m, 2H, NH), 4.59 (m, 2H, CH—$CO_2$Me), 3.77 (s, 6H, $CO_2CH_3$), 3.17 (d, J=4.7 Hz, CH—$CH_2$—S), 1.45 (s, 18H, $C(CH_3)_3$).

Synthesis of dimethyl 3,3'-disulfidediyl(2R,2'R)-bis (2-(((benzyloxy)carbonyl) amino)propanoate) D-n

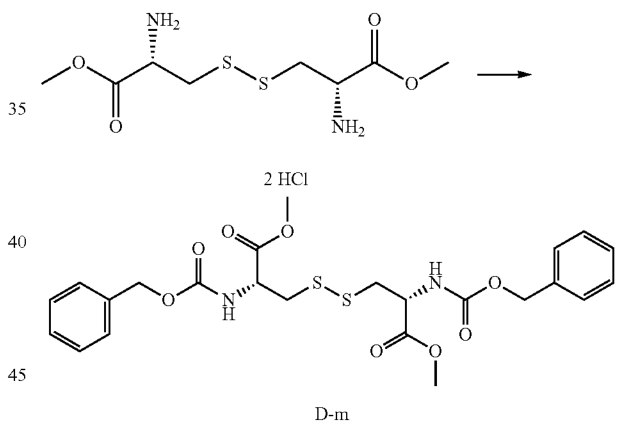

D-m

Disulfide D-n was synthesized according to a literature known procedure (cf. L. Liu, S. Tanke, M. J. Miller, 1986, 51, 5332-5337). The pure product was obtained by washing the oily residue with a mixture of ethyl acetate/n-hexane (v/v 1:2, 40 mL) via ultrasonic irradiation. The product separated as an oil and the wash solution was decanted. The colourless oily residue solidified over several days at rt (3.73 g, 6.95 mmol, 70%). The analytical data are consistent with those from the above literature.

Melting point: 65-68° C. (Lit.: 68-69° C.). $^1H$-NMR (300 MHz, $CDCl_3$): δ (ppm)=7.35 (s, 10H, Ar—H), 5.65 (m, 2H, NH), 5.12 (s, 4H, Ar—$CH_2$), 4.68 (m, 2H, $CHCO_2$Me), 3.75 (s, 6H, $CH_3$), 3.16 (d, J=4.9 Hz, 4H, $CH_2$—S).

Example 1: Investigation of Different N-Heterocyclic Carbenes for Sulfur Extrusion The sulfur extrusion from a disulfide compound D-a to the corresponding thioether compound T-a was investigated for four different commercially available NHCs. For this purpose, sodium hydride as a non-nucleophilic base was added in a slight excess to generate the carbene from the corresponding imidazolium salt. The reaction was carried out in THE at 50° C. for 24h in accordance with the general procedure described above. The obtained results are summarized in Table 1.

Scheme 2: Investigation of different NHCs (Table 1).

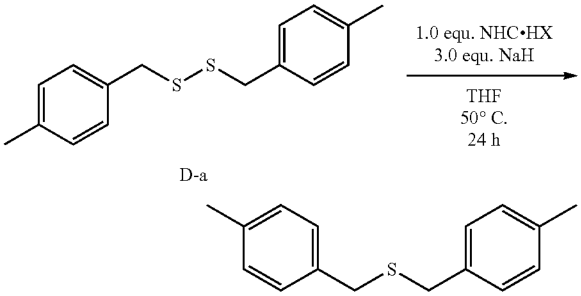

D-a

T-a

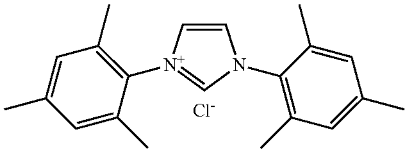

IMes•HCl

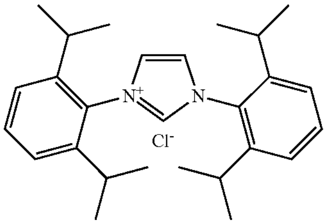

IPr•HCl

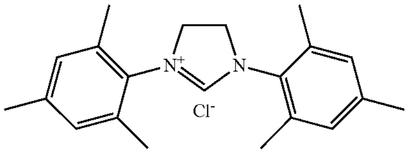

sIMes•HCl

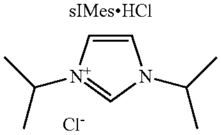

NHC-4

TABLE 1

| Investigation of different NHCs. | | | |
|---|---|---|---|
| Entry | NHC salt | NMR yield [%][a)] | Conversion [%][a)] |
| 1 | IMes•HCl | 69 | 100 |
| 2 | IPr•HCl | 42 | 75 |
| 3 | sIMes•HCl | 68 | 89 |
| 4 | NHC-4 | 63 | 98 |
| 5 | None | — | — |
| 6 | IMes•HCl[b)] | — | — |
| 7 | IMes[c)] | 67 | 76 |

[a)]NMR yield/conversion determined using 1,3,5-trimethoxy benzene (TMB) as an internal standard,
[b)]no base added,
[c)]Free carbene used in place of IMes•HCl.

The most nucleophilic NHCs IMes-HCl and SIMes-HCl lead to the highest yields of 69% and 68%, respectively (Entries 1 and 3). Using the sterically more hindered IPr-HCl (Entry 2) a lower yield of 42% was obtained, despite its nucleophilicity being similar to IMes-HCl. The smaller carbene NHC-4 with a moderate nucleophilicity leads to 63% yield (Entry 4). Moreover, reaction controls without imidazolium salt (Entry 5), without base (Entry 6) and with the free carbene (Entry 7) confirm the role of the NHC as the nucleophile mediating the reaction.

Example 2: Investigation of Different Bases Used for Generating Free NHCs for Sulfur Extrusion from the Corresponding Protonated Salts Different bases were used for carbene generation and the results on the sulfur extrusion from compound D-a to compound T-a, which were carried out in accordance with the above general procedure, are summarized in Table 2.

Scheme 3: Investigation of different bases (Table 2).

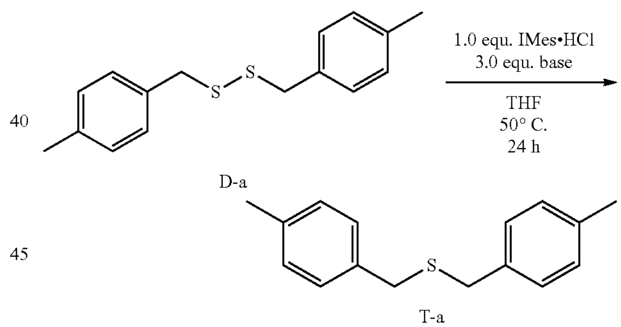

D-a

T-a

TABLE 2

| Investigation of different bases. | | | |
|---|---|---|---|
| Entry | Base | NMR yield [%][a)] | Conversion [%][a)] |
| 1 | NaH | 52 | 96 |
| 2 | $Cs_2CO_3$ | 61 | 95 |
| 3 | $K_2CO_3$ | 66 | 99 |
| 4 | DBU | 41 | 76 |

[a)]NMR yield/conversion determined using 1,3,5-trimethoxy benzene (TMB) as an internal standard.

As demonstrated in the above Table 2, sodium hydride and mild carbonates showed high yields. When compared to sodium hydride (Entry 1), the mild carbonates (Entries 2 and 3), which can be handled more easily, increased the yield. The results for DBU further showed that organic bases may also be used (Entry 4).

Example 3: Investigation of Different Solvents Used During Sulfur Extrusion

The applicability of different solvents for sulfur extrusion was investigated, thereby using potassium carbonate and sodium hydride as bases. The reactions were carried out in accordance with the general procedure described above and the obtained results are summarized in Table 3.

Scheme 4: Investigation of different solvents (Table 3).

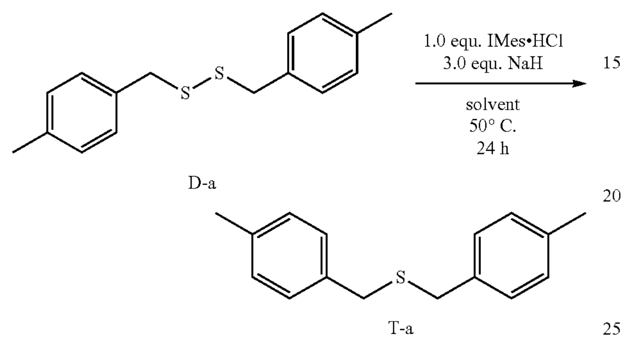

D-a

T-a

TABLE 3

Investigation of different solvents.

| Entry | Base | Solvent | NMR yield [%][a)] | Consumption [%][a)] |
|---|---|---|---|---|
| 1 | $K_2CO_3$ | DMF | 62 | 93 |
| 2 | $K_2CO_3$ | acetonitrile | 67 | 86 |
| 3 | $K_2CO_3$ | THF | 67 | 85 |
| 4 | $K_2CO_3$ | toluene | 54 | 93 |
| 5 | $K_2CO_3$ | n-hexane | 53 | 68 |
| 6 | $K_2CO_3$ | methanol | 64 | 67 |
| 7 | $K_2CO_3$ | ethanol | 67 | 99 |
| 8 | $K_2CO_3$ | isopropanol | 73 | 99 |
| 9 | NaH | DMF | 63 | 98 |
| 10 | NaH | acetonitrile | 67 | 100 |
| 11 | NaH | THF | 52 | 99 |
| 12 | NaH | toluene | 72 | 88 |
| 13 | NaH | n-hexane | 68 | 94 |

[a)]NMR yield determined using 1,3,5-trimethoxy benzene (TMB) as an internal standard.

As demonstrated by the above results, both polar and non-polar, aprotic solvents are suitable for the sulfur extrusion and lead to similar NMR yields from 53% to 67%. Moreover, greener solvents, which may be applied in biochemistry, as ethanol and isopropanol also gave yields of 67% and 73%, respectively. These results verify the high versatility of the NHC induced sulfur extrusion where the solvent can be adapted to the reacting disulfide as required.

Example 4: Investigations Concerning Further Reactions Conditions

Using IMes-HCl as NHC salt and NaH as base, further reaction conditions (concentration, amount of NHC, and temperature) were investigated. The results are shown in Table 4.

Scheme 5: Investigations concerning further reaction conditions (Table 4).

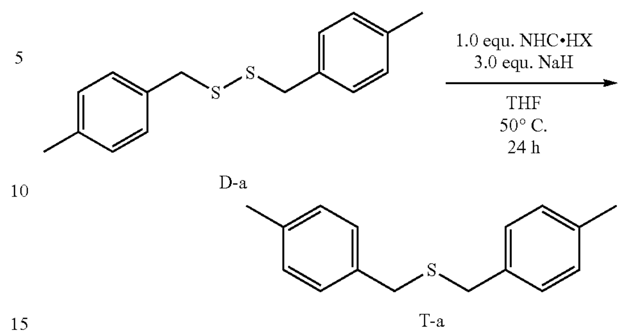

D-a

T-a

TABLE 4

Investigations concerning further reaction conditions.

| Entry | Variation | NMR yield [%][a)] | Conversion [%][a)] |
|---|---|---|---|
| 1 | 1.5 mL THF | 46 | 99 |
| 2 | None (3.0 mL THF, 1.0 equ. NHC•HCl, 50° C.) | 52 | 96 |
| 3 | 6.0 mL THF | 30 | 47 |
| 4 | 12 mL THF | 22 | 85 |
| 5 | 1.3 equ. IMes•HCl | 64 | 99 |
| 6 | 1.5 equ. IMes•HCl | 84 | 100 |
| 7 | 2.0 equ. IMes•HCl | 77 | 100 |
| 8 | Rt | 61 | 92 |

[a)]NMR yield/conversion determined using 1,3,5-trimethoxy benzene (TMB) as an internal standard.

As demonstrated by the above results, even when varying the concentration, the amount of NHC, and the temperature, sulfur extrusion can be carried out. Increasing the concentration lead to a smaller reduction of the NMR yield (Entry 1) as dilution (Entries 3 and 4) when comparing the same to the original result (Entry 2). Increasing the NHC stoichiometry to 1.5 equivalents resulted in higher yields, while additional amounts of IMes-HCl did not lead to further improvement (Entries 5-7). Furthermore, a decrease in temperature did not change the yield showing that the reaction can be performed at ambient conditions (Entry 8).

Example 5: Investigations Concerning the Substrate Scope

For investigating the scope of the sulfur extrusion, different substrates were applied. 10 benzylic substrates and one heterocyclic substrate were synthesized, sulfur extruded and the corresponding sulfides isolated.

The applied general procedure (GP3) was as follows:

1,3-bis(2,4,6-trimethylphenyl)-1H-imidazole-3-iumchloride (1.02 g, 3.00 mmol, 1.5 eq) and potassium carbonate (1.24 g, 9.00 mmol, 4.5 eq) were mixed in tetrahydrofuran (80 mL). Afterwards disulfide (549 mg, 2.00 mmol, 1.0 eq) was added and the reaction was stirred until completion of the reaction (usually 24 h) at rt. The solvent was removed under reduced pressure and the crude product was purified by column chromatography to obtain the sulfide. Minor impurities as disulfide residues were removed for analytical samples by HPLC, if indicated.

Bis(4-methylbenzyl)sulfide T-a

T-a

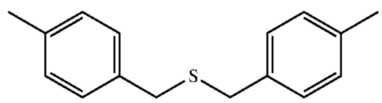

T-a was synthesized according to GP3. The sulfide was purified by column chromatography ($SiO_2$, PE:EE 20:1, $R_f$=0.83) to obtain the product as a colourless solid (470 mg, 1.94 mmol, 97%). The analytical data are consistent with those from literature (cf. K. S. Eccles, C. J. Elcoate, S. E. Lawrence, A. R. Maguire, Gen. Pap. Ark. 2010, ix, 216-228).

Melting point: 69° C. (Lit.: 76-78° C.). $^1$H NMR (300 MHz, $CDCl_3$): δ (ppm)=7.14 (m, 8H, Ar—H), 3.57 (s, 4H, Ar—$CH_2$—S), 2.34 (s, 6H, $CH_3$). $^{13}$C NMR (75 MHz, $CDCl_3$): δ (ppm)=136.7, 135.3, 129.3, 129.0, 35.4, 21.3. FT-IR (ATR): ṽ ($cm^{-1}$)=3126 (vw), 3089 (vw), 3048 (w), 3021 (w), 2954 (m), 2921 (m), 2855 (m), 2733 (vw), 1906 (w), 1802 (vw), 1725 (w), 1705 (w), 1664 (vw), 1610 (w), 1575 (vw), 1511 (m), 1456 (w), 1428 (w), 1415 (m), 1378 (w), 1317 (w), 1258 (w), 1234 (w), 1212 (w), 1201 (w), 1178 (w), 1109 (m), 1040 (m), 1021 (m), 963 (w), 897 (vw), 817 (vs), 750 (m), 727 (s), 699 (w), 679 (m), 660 (w), 642 (vw). HRMS (El, pos): m/z calcd. for [$M^+$]: 242.1129, found: 242.1111 (23), 137.0413 (14), 105.0698 (100), 77.0387 (13). Elemental analysis: Calcd. for $C_{16}H_{18}S$: C, 79.29, H, 7.49; found: C, 79.10, H, 7.33.

Bis(4-methoxybenzyl)sulfide T-b

T-b

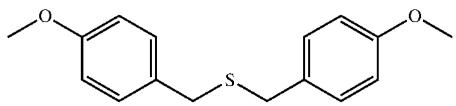

T-b was synthesized according to GP3. The sulfide was purified by column chromatography ($SiO_2$, PE:EE 20:1, $R_f$=0.20) to obtain the product as a colourless solid (499 mg, 1.82 mmol, 91%). The analytical data are consistent with those from literature (Y. A. W. Park, Y. Na, D. J. Baek, Bull. Korean Chem. Soc. 2006, 27, 2023-2027).

Melting point: 30° C. (Lit.: 30° C.). $^1$H NMR (400 MHz, $CDCl_3$): δ (ppm)=7.22-7.19 (m, 4H, Ar—H), 6.87-6.83 (m, 4H, Ar—H), 3.81 (s, 6H, $OCH_3$), 3.56 (s, 4H, Ar—$CH_2$—S). $^{13}$C NMR (100 MHz, $CDCl_3$): δ (ppm)=159.2, 130.7, 129.6, 114.1, 55.4, 43.0. FT-IR (ATR): ṽ ($cm^{-1}$)=3067 (vw), 3008 (w), 2957 (w), 2933 (w), 2837 (w), 2052 (vw), 1989 (vw), 1888 (w), 1768 (vw), 1650 (vw), 1608 (m), 1582 (w), 1507 (vs), 1466 (m), 1457 (m), 1443 (m), 1417 (m), 1316 (w), 1301 (m), 1242 (vs), 1172 (s), 1106 (m), 1029 (s), 953 (vw), 939 (vw), 902 (vw), 828 (vs), 765 (w), 748 (m), 737 (m), 679 (m), 663 (w), 636 (w). HRMS (El, pos): m/z calcd. for [$M^+$]: 274.1028, found: 274.1012 (12), 121.0643 (100). Elemental analysis: Calcd. for $$C_{16}H_{18}O_2S \cdot \frac{1}{11} EtOAc$$

C, 69.69, H, 6.68; found: C, 69.57, H, 6.65.

Bis(4-bromobenzyl)sulfide T-c

T-c

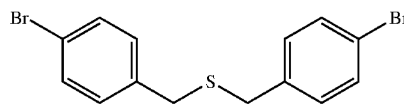

T-c was synthesized according to GP3. The sulfide was purified by column chromatography ($SiO_2$, PE:DCM 10:1, $R_f$=0.36) to obtain the product as a colourless solid (45.6 mg, 123 μmol, 35%). The analytical data are consistent with those from literature (cf. C. G. Overberger, R. A. Gadea, J. A. Smith6, I. C. Kogon, *J. Am. Chem. Soc.* 1953, 75, 2075-2077).

Melting point: 51° C. (Lit.: 59-60° C.). $^1$H NMR (400 MHz, $CDCl_3$): δ (ppm)=7.47 (d, J=8.3 Hz, 4H, Ar—H), 7.19 (d, J=8.3 Hz, 4H, Ar—H), 3.58 (s, 4H, Ar—$CH_2$—S). $^{13}$C NMR (100 MHz, $CDCl_3$): δ (ppm)=137.9, 132.0, 131.3, 121.3, 35.6. FT-IR (ATR): ṽ ($cm^{-1}$)=3084 (vw), 3061 (vw), 3048 (vw), 3026 (vw), 2959 (vw), 2923 (w), 2912 (w), 2851 (vw), 2816 (vw), 2782 (vw), 2657 (vw), 2614 (vw), 2594 (vw), 2559 (vw), 2551 (vw), 2478 (vw), 2439 (vw), 2403 (vw), 2371 (vw), 2311 (vw), 2281 (vw), 2232 (vw), 1983 (vw), 1953 (vw), 1904 (w), 1783 (vw), 1725 (vw), 1709 (vw), 1660 (w), 1586 (w), 1483 (s), 1443 (w), 1415 (w), 1400 (m), 1351 (vw), 1304 (vw), 1280 (vw), 1250 (vw), 1231 (w), 1198 (w), 1172 (w), 1157 (vw), 1140 (vw), 1097 (w), 1069 (s), 1038 (w), 1009 (s), 957 (w), 884 (w), 826 (vs), 804 (s), 752 (m), 724 (m), 693 (w), 680 (w), 646 (w), 630 (w), 626 (w), 609 (m). HRMS (El, pos): m/z calcd. for [$M^+$]: 371.9006, found: 371.8987 (20), 168.9641 (100), 122.0179 (10), 90.0461 (20). Elemental analysis: Calcd. for $C_{14}H_{12}Br_2S$: C, 45.19, H, 3.25; found: C, 45.45, H, 3.55.

Dimethyl 4,4'-(thiobis(methylene))dibenzoate T-d

T-d

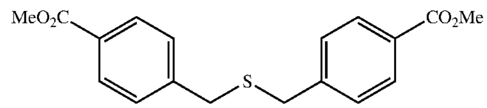

T-d was synthesized according to GP3 but the reaction time was extended to three days. The sulfide was purified by column chromatography ($SiO_2$, PE:EE 2:1, $R_f$=0.35).

In this case the sulfide was difficult to isolate from the thiourea side product. Final purification was achieved by NP-HPLC (DCM:EE 9:1, 20 mL $min^{-1}$, $R_t$=3.4 min) and the sulfide (238 mg, 720 μmol, 36%) was isolated.

Melting point: 93° C. $^1$H NMR (400 MHz, $CDCl_3$): δ (ppm)=7.98 (d, J=8.4 Hz, 4H, Ar-2-H), 7.33 (d, J=8.4 Hz, 4H, Ar-3-H), 3.92 (s, 6H, $CO_2CH_3$), 3.61 (s, 4H, Ar—$CH_2$—S). $^{13}$C NMR (100 MHz, $CDCl_3$): δ (ppm)=167.0 (Ar—$CO_2$Me), 143.3 (Ar—C-4), 130.0 (Ar—C-2/6), 129.2 (Ar—C-1), 129.2 (Ar—C-3/5), 52.3 ($CO_2CH_3$), 35.5 (Ar—$CH_2$—S). FT-IR (ATR):

ṽ ($cm^{-1}$)=3035 (vw), 3007 (vw), 2960 (w), 2939 (w), 2910 (vw), 2851 (vw), 2119 (vw), 2074 (vw), 1952 (vw), 1936 (vw), 1925 (vw), 1712 (s), 1606 (m), 1573 (w), 1505 (vw), 1440 (m), 1419 (m), 1406 (w), 1305 (m), 1275 (vs), 1212 (w), 1197 (m), 1172 (m), 1150 (m), 1114 (s), 1103 (s), 1015 (m), 983 (vw), 965 (m), 915 (w), 860 (m), 837 (w), 796 (w), 771 (m), 727 (vs), 689 (m), 636 (w), 619 (w). HRMS (EI, pos): m/z calcd. for [$M^+$]: 330.0926, found: 330.0924 (40), 299.0741 (14), 181.0328 (15), 149.0608 (100), 121.0662 (27), 90.0471 (18). Elemental analysis: Calcd. for $C_{18}H_{18}O_4S$: C, 65.44, H, 5.49; found: C, 65.02, H, 5.69.

Synthesis of bis(4-trifluoromethylbenzyl)sulfide T-e

T-e

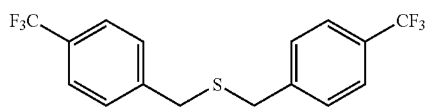

T-e was synthesized according to GP3. The sulfide was purified by column chromatography ($SiO_2$, PE:EE 20:1, $R_f$=0.34) to obtain the product as a colourless oil in satisfying purity (210 mg, 600 μmol, 30%). Higher purification was achieved by NP-HPLC (DCM:n-hexane, 20 mL $min^{-1}$, $R_t$=4.0 min). The analytical data are consistent with those from literature (cf. G. Buehrdel, E. Petrlikova, P. Herzigova, R. Beckert, H. Goerls, *Phosphorus, Sulfur Silicon Relat. Elem.* 2009, 184, 1161-1174).

$^1$H NMR (400 MHz, $CDCl_3$): δ (ppm)=7.59 (d, J=8.1 Hz, 4H, Ar—H), 7.33 (d, J=8.1 Hz, 4H, Ar—H), 3.65 (s, CH2). $^{13}$C NMR (100 MHz, $CDCl_3$): δ (ppm)=141.9, 129.3, 129.2, 125.5 (q), 126.2 (q), 36.1. FT-IR (ATR): ṽ ($cm^{-1}$)=3071 (vw), 3046 (vw), 3020 (vw), 2926 (vw), 2855 (vw), 1922 (vw), 1803 (vw), 1710 (w), 1618 (w), 1584 (vw), 1514 (vw), 1420 (w), 1321 (vs), 1236 (w), 1162 (s), 1119 (s), 1104 (s), 1066 (vs), 1018 (s), 955 (vw), 896 (w), 849 (m), 754 (w), 709 (w), 616 (w). HRMS (EI, pos): m/z calcd. for $C_{16}H_{12}F6S$ [$M^+$]: 350.0564, found 350.0559 (30), 191.0137 (21), 159.0416 (100), 109.0454 (12). Elemental analysis: Calcd. for $C_{16}H_{12}F_6S$.1/6 THF: C, 55.27, H, 3.66; found: C, 55.21, H, 3.81.

Bis(3-methoxybenzyl)sulfide T-f

T-f

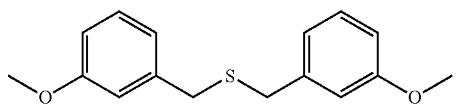

T-f was synthesized according to GP3. The sulfide was purified by column chromatography ($SiO_2$, PE:EE 20:1, $R_t$=0.23) to obtain the product as a colourless oil (417 mg, 1.52 mmol, 76%). The analytical data are consistent with those from literature (cf. K. S. Eccles, C. J. Elcoate, S. E. Lawrence, A. R. Maguire, *Gen. Pap. Ark.* 2010, ix, 216-228).

$^1$H NMR (400 MHz, $CDCl_3$): δ (ppm)=7.15 (t, J=7.81 Hz, 2H, Ar—H), 6.81-6.78 (m, 4H, Ar—H), 6.72 (m, 2H, Ar—H), 3.73 (s, 6H, $OCH_3$), 3.52 (s, 4H, Ar—$CH_2$—S). $^{13}$C NMR (100 MHz, $CDCl_3$): δ (ppm)=159.9, 139.9, 129.6, 121.6, 114.6, 112.8, 55.4, 35.8. FT-IR (ATR): ṽ ($cm^{-1}$) =3052 (w), 2999 (w), 2957 (w), 2939 (w), 2913 (w), 2833 (w), 2093 (vw), 2073 (vw), 2037 (vw), 1999 (vw), 1930 (vw), 1888 (vw), 1843 (vw), 1599 (s), 1583 (s), 1489 (s), 1465 (m), 1453 (m), 1436 (m), 1314 (m), 1297 (m), 1262 (vs), 1189 (w), 1150 (s), 1089 (w), 1078 (w), 1041 (s), 995 (w), 934 (w), 915 (w), 874 (m), 781 (s), 747 (m), 737 (m), 711 (m), 690 (s). HRMS (EI, pos): m/z calcd. for [$M^+$]: 274.1028, found: 274.1028 (10), 138.0677 (16), 122.0727 (100), 109.0648 (17), 91.0544 (29), 77.0383 (18). Elemental analysis: Calcd. for $C_{16}H_{13}O_2S$: C, 70.04, H, 6.61; found: C, 70.18, H, 6.58.

Dimethyl 3,3'-(thiobis(methylene))dibenzoate T-g

T-g

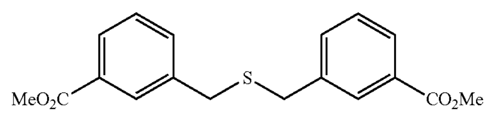

T-g was synthesized according to GP3 but the reaction time was extended to three days. The sulfide was purified by column chromatography ($SiO_2$, PE:EE 2:1, $R_t$=0.35) to obtain the product as colourless needles (515 mg, 1.56 mmol, 78%).

Melting point: 90-93° C. $^1$H NMR (400 MHz, $CDCl_3$): δ (ppm)=7.93-7.91 (m, 4H, Ar-2/6-H), 7.48-7.46 (m, 2H, Ar-4-H), 7.38 (t, J=7.9 Hz, 2H, Ar-5-H), 3.92 (s, 6H, $CO_2CH_3$), 3.64 (s, 4H, Ar—$CH_2$—S). $^{13}$C NMR (100 MHz, $CDCl_3$): δ (ppm)=167.0 ($CO_2$Me), 138.5 (Ar—C-3), 133.6 (Ar—C-2), 130.6 (Ar—C-1), 130.2 (Ar—C-4), 128.8 (Ar—C-5), 128.5 (Ar—C-6), 52.3 ($CO_2CH_3$), 35.6 (Ar—$CH_2$—S). FT-IR (ATR): ṽ ($cm^{-1}$)=3058 (vw), 2971 (w), 2958 (w), 2939 (w), 2928 (w), 2874 (vw), 2839 (vw), 2184 (vw), 2159 (vw), 2098 (vw), 2073 (vw), 1982 (vw), 1960 (vw), 1903 (vw), 1854 (vw), 1789 (vw), 1718 (vs), 1678 (w), 1638 (w), 1606 (w), 1585 (w), 1542 (vw), 1484 (w), 1458 (w), 1444 (m), 1379 (vw), 1283 (vs), 1231 (s), 1195 (s), 1143 (w), 1106 (m), 1084 (m), 1057 (w), 1041 (m), 992 (m), 934 (w), 908 (vw), 878 (w), 854 (w), 833 (w), 820 (w), 794 (w), 758 (s), 733 (w), 711 (s), 690 (m), 667 (w), 635 (vw). HRMS (EI, pos): m/z calcd. for [$M^+$]: 330.0926, found: 330.0904 (22), 299.0721 (10), 181.0322 (32), 149.0601 (100), 119.0489 (26), 91.0542 (29). Elemental analysis: Calcd. for $C_{18}H_{18}O_4S$: C, 65.44, H, 5.49; found: C, 65.56, H, 5.64.

Bis(3-trifluoromethylbenzyl)sulfide T-h

T-h

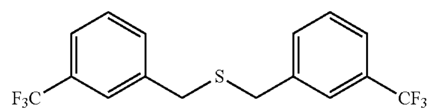

T-h was synthesized according to GP3. The sulfide was purified by column chromatography ($SiO_2$, PE:EE 20:1, $R_t$=0.50) to obtain the product as a colourless oil in satisfying purity (301 mg, 1.24 mmol, 62%). Higher purification was achieved by NP-HPLC (DCM:n-hexane, 20 mL $min^{-1}$, $R_t$=3.0 min).

$^1$H NMR (400 MHz, $CDC_3$): δ (ppm)=7.52-7.40 (m, 8H, Ar-3/4/5/7-H), 3.64 (s, 4H, Ar—$CH_2$—S). $^{13}$C NMR (100

MHz, $CDC_3$): δ (ppm)=139.0, 132.4, 131.1 (q), 129.2, 125.8 (q), 124.2 (q), 124.2 (q), 35.5. FT-IR (ATR): ṽ ($cm^{-1}$)=3112 (vw), 3066 (vw), 3047 (vw), 3023 (vw), 2921 (vw), 1960 (vw), 1901 (vw), 1612 (vw), 1596 (w), 1493 (w), 1449 (m), 1422 (w), 1329 (vs), 1234 (w), 1194 (m), 1162 (s), 1117 (vs), 1092 (s), 1072 (s), 1003 (w), 982 (vw), 934 (w), 904 (m), 886 (m), 828 (w), 801 (m), 759 (w), 732 (m), 699 (s), 659 (m), 629 (vw). HRMS (El, pos): m/z calcd. for [$M^+$]: 350.0564, found: 350.0551 (20), 191.0126 (17), 159.0405 (100), 109.0433 (20). Elemental analysis: Calcd. for $C_{16}H_{12}F_6S$.1/7 THF: C, 55.19, H, 3.67; found: C, 55.19, H, 3.85.

Bis((perfluorophenyl)methyl)sulfide T-i

T-i

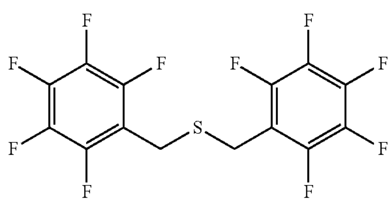

T-i was synthesized according to GP3. The sulfide was purified by column chromatography ($SiO_2$, PE:DCM 40:1, $R_f$=0.24) to obtain the product as a colourless solid in satisfying purity (37.3 mg, 94.5 μmol, 27%). Higher purification was achieved by NP-HPLC (DCM, 20 mL $min^{-1}$, Rt=3.4 min).

Melting point: 58-62° C. 1H NMR (300 MHz, $CDCl_3$): δ (ppm)=3.86 (s, 4H, Ar—$CH_2$—S). $^{13}C$ NMR (150 MHz, $CDCl_3$): δ (ppm)=145.1 (md, Ar—C-3), 140.9 (md, Ar—C-4), 137.8 (md, Ar—C-2), 122.2 (dt, Ar—C-1), 23.9 (Ar—$CH_2$—S). FT-IR (ATR): ṽ ($cm^{-1}$)=2948 (vw), 2931 (vw), 2647 (vw), 2433 (vw), 2409 (vw), 2117 (vw), 2087 (vw), 2071 (vw), 1899 (vw), 1860 (vw), 1719 (vw), 1657 (w), 1520 (m), 1499 (vs), 1430 (w), 1415 (w), 1365 (vw), 1311 (w), 1289 (vw), 1254 (vw), 1244 (vw), 1192 (w), 1171 (w), 1123 (s), 1036 (w), 987 (s), 962 (vs), 920 (w), 890 (m), 877 (w), 773 (vw), 752 (w), 714 (w), 699 (w), 655 (w), 645 (w), 602 (w). HRMS (El, pos): m/z calcd. for [M*]: 393.9874, found: 393.9879 (10), 181.0061 (100). Elemental analysis: Calcd. for: C, 42.65, H, 1.02; found: C, 42.37, H, 1.41.

Bis(2,4,6-trimethylbenzyl)sulfide T-j

T-j

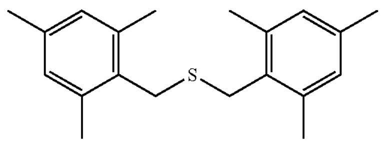

T-j was synthesized according to GP3. The sulfide was purified by column chromatography ($SiO_2$, PE:methyl tert butylether 10:1, $R_f$=0.73) to obtain the product as a colourless solid (89.8 mg, 301 μmol, 86%).

Melting point: 140° C. $^1H$ NMR (300 MHz, $CDCl_3$): δ (ppm)=6.81 (s, 4H, Ar-3-H), 3.76 (s, 4H, Ar—$CH_2$—S), 2.33 (s, 12H, Ar-2/6-H), 2.24 (s, 6H, Ar-4-H). $^{13}C$ NMR (75 MHz, $CDCl_3$): δ (ppm)=137.1 (Ar—C-2), 136.5 (Ar—C-4), 131.2 (Ar—C-1), 129.1 (Ar—C-3), 31.1 (Ar—$CH_2$—S), 21.0 (Ar-4-$CH_3$), 19.6 (Ar-2/6-$CH_3$). FT-IR (ATR): ṽ ($cm^{-1}$)=3006 (w), 2963 (m), 2945 (w), 2909 (w), 2856 (w), 2727 (vw), 2468 (vw), 2392 (vw), 2359 (vw), 2331 (vw), 2059 (vw), 1999 (vw), 1947 (vw), 1908 (vw), 1883 (vw), 1754 (vw), 1723 (w), 1611 (m), 1578 (w), 1543 (w), 1503 (w), 1480 (m), 1458 (m), 1440 (m), 1422 (m), 1371 (m), 1243 (vw), 1216 (w), 1190 (m), 1140 (w), 1031 (m), 1013 (m), 948 (w), 872 (w), 848 (vs), 801 (w), 752 (w), 692 (s). HRMS (El, pos): m/z calcd. for $C_{20}H_{26}S$ [$M^+$]: 298.1755, found: 298.1755 (15), 133.1007 (100). Elemental analysis: Calcd. for $C_{20}H_{26}S$: C, 80.48, H, 8.78; found: C, 80.47, H, 8.79.

Bis(furan-2-ylmethyl)sulfide T-k

T-k

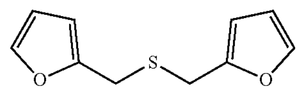

T-k was synthesized according to GP3. The sulfide was purified by filtration over a silica plug (8 cm, $SiO_2$, PE:EE 20:1) to obtain the product with minor impurities (95%). The sulfide was found to be sensitive if exposed to light and rt for several hours. Therefore, further purification was achieved by NP-HPLC (DCM:n-hexane 2:1, 20 mL $min^{-1}$, $R_t$=6.8 min). The analytical data are consistent with those from literature (cf. S. C. A. Sousa, J. R. Bernardo, M. Wolff, B. Machura, A. C. Femandes, *European J. Org. Chem.* 2014, 2014, 1855-1859).

$^1H$ NMR (400 MHz, $CDCl_3$): δ (ppm)=7.37 (dd, J=1.8 Hz, 0.7 Hz, 2H, Ar—H), 6.32 (dd, J=3.1 Hz, 1.9 Hz, 2H, Ar—H), 6.20 (d, J=3.1 Hz, 2H, Ar—H), 3.70 (s, 4H, Ar—$CH_2$—S). $^{13}C$ NMR (100 MHz, $CDCl_3$): δ (ppm)=151.5, 142.4, 110.5, 107.9, 27.9. FT-IR (ATR): ṽ ($cm^{-1}$)=3061 (vw), 3028 (w), 2998 (w), 2951 (w), 2842 (w), 2080 (vw), 1988 (vw), 1965 (vw), 1905 (vw), 1717 (vs), 1606 (w), 1589 (w), 1485 (w), 1445 (m), 1433 (m), 1305 (m), 1283 (vs), 1223 (s), 1199 (s), 1104 (s), 1079 (m), 988 (m), 916 (w), 872 (w), 819 (w), 794 (m), 757 (s), 717 (m), 699 (s), 674 (m), 660 (w). HRMS (El, pos): m/z calcd. for [$M^+$]: 194.0402, found:194.0386 (12), 126.0129 (10), 113.0045 (16), 81.0330 (100), 53.0386 (24). Elemental analysis: Calcd. for $C_{10}H_{10}O_2S$: C, 61.83, H, 5.19; found: C, 61.91, H, 5.45.

In an effort to delineate the electronic contribution of the aryl ring to the reaction progress, various para- and meta substituted benzylic disulfides were examined. The results are summarized in Table 5.

Scheme 6: Substrate scope of the sulfur extrusion reaction (Table 5).

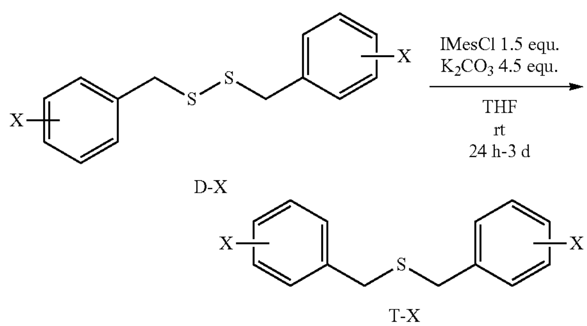

D-X

T-X

TABLE 5

Substrate scope of the sulfur extrusion reaction.

| Entry | Substituent | Yield [%][a)] |
|---|---|---|
| 1 | 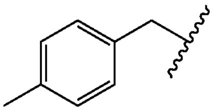 T-a | 97 |
| 2 | 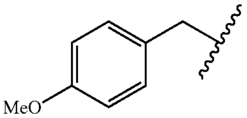 T-b | 91 |
| 3 | 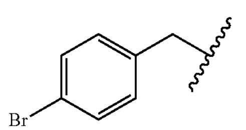 T-c | 35 |
| 4 | 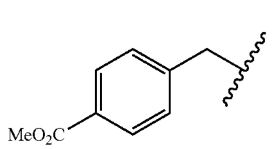 T-d | 36[b),c)] |
| 5 | 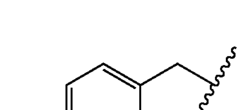 T-e | 30 |
| 6 | 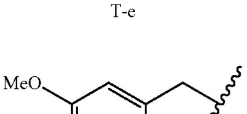 T-f | 76 |
| 7 | 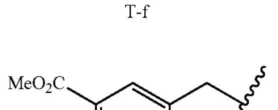 T-g | 86[c)] |
| 8 | 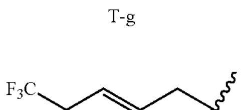 T-h | 62 |
| 9 | 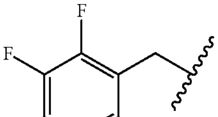 T-i | 27 |
| 10 | 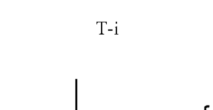 T-j | 86 |
| 11 | 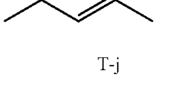 T-k | 95 |

[a)]Yields are isolated yields and averaged over two experiments.
[b)]HPLC was used to separate sulfide from thiourea,
[c)]reaction time 3 d.

Substrates having p-Me and p-OMe substituents (Entries 1 and 2) delivered 97% and 91% yield, respectively. A p-Br substituent (Entry 3) lead to a slightly lower yield of 35%. Electron withdrawing groups as p-$CO_2Me$ and p-$CF_3$ (Entries 4 and 5) lead to 36% and 30% yield, respectively. In general, the para substituted substrates reveal that compounds having more electron rich substituents react much faster than those with electron poor substituents. In comparison, the corresponding meta substituted substrates show the same general trend with decreasing electron density but behave different to their para isomers. The yield of p-OMe to m-OMe (Entries 2 and 6) dropped slightly from 91% to 76%, in good agreement with the reduced σ-value of m-OMe with regard to p-OMe. The electron withdrawing groups m-$CO_2Me$ and m-$CF_3$ (Entries 7 and 8) lead to 86% and 62% isolated yield, respectively, which are higher than for their para-substituted analogues, as their σ-values would suggest.

Moreover, steric influences were investigated. For this purpose, the 2,4,6-trimethylphenyl compound D-j was utilised and a high yield of 86% was isolated for the thioether T-j (Entry 10), which indicated that the steric impact is minimal in this reaction. Moreover, pentafluorobenzyl disulfide D-i was submitted to the reaction conditions, leading to a 27% yield of T-i (Entry 9), indicating both an electronic and steric influence. When comparing T-i and T-j it becomes clear that electronic effects have a greater influence on the efficiency of the sulfur extrusion than steric effects from the aromatic ring. Furthermore, a commercially available furyl disulfide D-k was extruded to obtain 95% yield of thioether T-k, showing that heterocycles are subjectable to sulfur extrusion as well.

In an effort to extend the scope towards non-benzyl substituted disulfides, ester D-I was tested (cf. Scheme 7 below). The reaction proceeded smoothly and 64% of sulfide T-I were obtained. Moreover, two cystine derivatives D-m and D-n were tested as a model compound for peptidic residues. The sulfur extrusion of D-m/n lead to two products which were the desired lanthionine derivatives T-m/n in 28 and 48% yield, respectively, and the corresponding dehydroalanine derivatives A-m/n in 17 and 35% yield, respectively. The obtained results prove an easy access of lanthionine units from cystine under mild conditions which can be applied in the synthesis of lantibiotics such as Nisin that was synthesized with HMPA in the past.

Scheme 7: Further disulfides compatible with sulfur extrusion.

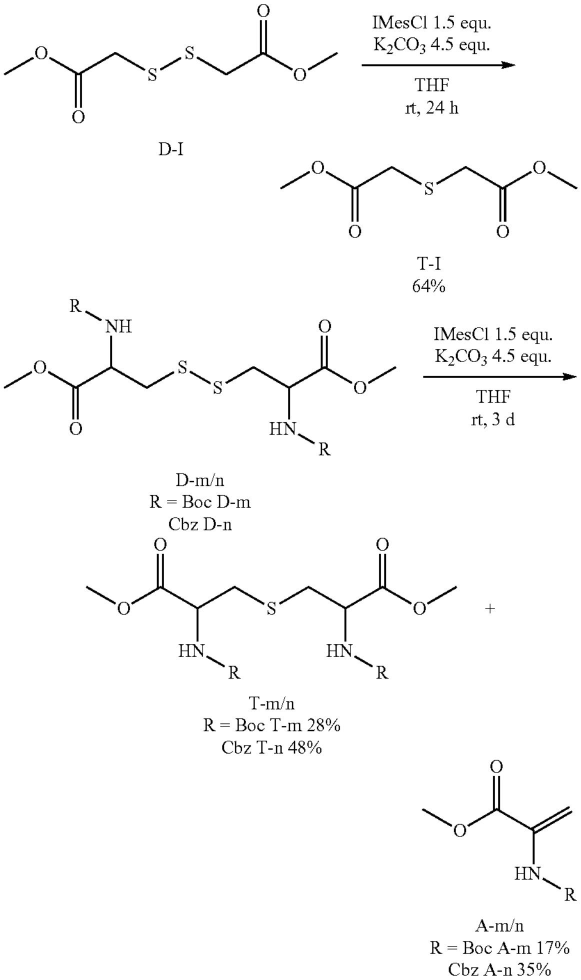

Dimethyl 2,2'-thiodiacetate T-1

T-1

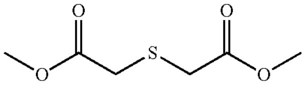

T-1 was synthesized according to GP3. The sulfide was purified by bulb-to-blub distillation (70° C., 10-3 mbar) and obtained as a colourless oil (64%). The analytical data are consistent with those from literature (cf. N. Agarwal, C.-H. Hung, M. Ravikanth, *Tetrahedron* 2004, 60, 10671-10680).

$^1H$ NMR (300 MHz, $CDCl_3$): δ (ppm)=3.74 (s, $CO_2CH_3$), 3.39 (s, $CH_2$). $^{13}C$ NMR (75 MHz, $CDCl_3$): δ (ppm)=170.4, 52.6, 33.6. FT-IR (ATR): ṽ ($cm^{-1}$)=3002 (w), 2955 (w), 2845 (vw), 1733 (vs), 1436 (s), 1411 (w), 1392 (w), 1276 (s), 1194 (m), 1153 (s), 1126 (s), 1005 (s), 930 (w), 879 (w), 833 (w), 772 (w), 708 (w). HRMS (El, pos): m/z calcd. for [$M^+$]: 178.0300, found: 178.0291 (12), 163.0976 (91), 146.0021 (65), 134.0953 (100), 120.0804 (56), 87.0429 (94). Elemental analysis: Calcd. for $C_{10}H_{10}O_2S$: C, 40.44, H, 5.66; found: C, 40.66, H, 5.76.

Dimethyl 3,3'-thiobis(2-((tert-butoxycarbonyl) amino)propanoate)) T-m

T-m

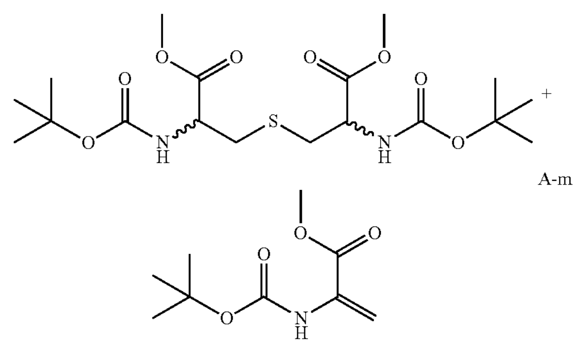

T-m was synthesized according to GP3. The sulfide was filtrated over a silica plug (8 cm, $SiO_2$, ethyl acetate) followed by ultrasonication in acetonitrile (3 mL). The resulting solution was decanted and further purified by RP-HPLC (MeCN, rt, 10 mL $m^{-1}$, R, =6.50 min (T-m), $R_f$=7.38 min (A-m), $R_f$=8.00 min (NHC-thiourea)) to obtain the pure product T-m as a colourless oil which solidified over several days at room temperature to a colourless solid (42.8 mg, 98.0 μmol, 28%), whereas A-m was isolated as a yellow oil (23.2 mg, 116 μmol, 17%).

T-m: $^1H$ NMR (400 MHz, $CDCl_3$): δ (ppm)=5.37 (m, 2H, NH), 4.50 (m, 2H, CH—$CO_2Me$) 3.74 (s, 6H, $CO_2CH_3$), 2.97 (m, 4H, S—$CH_2$—CH), 1.43 (s, 18H, OC($CH_3$)3). $^{13}C$ NMR (100 MHz, $CDC_3$): δ (ppm)=171.4 ($CO_2Me$), 155.3 (NHC═O), 80.3 (OC($CH_3$)3), 55.4 (CH—$CO_2Me$), 52.7 ($CO_2CH_3$), 35.4 (S—$CH_2$—CH), 28.39 (OCC$H_3$). FT-IR (ATR): ṽ (cm−$^1$)=3435 (vw), 3392 (vw), 3369 (vw), 3001 (vw), 2978 (w), 2961 (w), 2934 (w), 2874 (vw), 2849 (vw), 1745 (m), 1699 (s), 1503 (m), 1454 (w), 1437 (w), 1393 (w), 1367 (m), 1350 (m), 1316 (w), 1266 (m), 1248 (m), 1213 (m), 1159 (vs), 1053 (m), 1015 (m), 987 (w), 917 (w), 860 (w), 778 (w), 759 (w), 709 (vw). HRMS (ESI, DCM/MeOH, pos): m/z calcd. for [M+$Na^+$]: 459.1772, found: 459.1775 [M+$Na^+$] (100), 475.1515 [M+$K^+$] (20), 895.3662 [2M+$Na^+$] (17). Elemental analysis: Calcd. for $C_{18}H_{32}O_8N_2S$: C, 49.53, H, 7.39, N, 6.42; found: C, 49.35, H, 7.32, N, 6.51.

A-m: $^1H$ NMR (400 MHz, $CDCl_3$): δ (ppm)=7.00 (s, 1H, NH), 6.15 (s, 1H, E-$CH_2$), 5.73 (d, J=1.4 Hz, 1H, Z—$CH_2$), 3.83 (s, 3H, $CO_2CH_3$), 1.48 (s, 9H, OC($CH_3$)3. $^{73}C$ NMR (100 MHz, $CDCl_3$): δ (ppm)=164.6 ($CO_2Me$), 152.7 (NHC═O), 131.5 (C═$CH_2$), 105.3 (C═$CH_2$), 80.9 (OC ($CH_3$)3), 53.0 ($CO_2CH_3$), 28.4 (OC($CH_3$)3). FT-IR (ATR): ṽ

$(cm^{-1})$=3461 (vw), 3422 (w), 3401 (vw), 3340 (vw), 2980 (w), 2958 (w), 2934 w), 2874 (vw), 2855 (vw), 1782 (w), 1715 (s), 1634 (w), 1509 (s), 1441 (m), 1393 (w), 1368 (m), 1326 (s), 1244 (m), 1204 (m), 1153 (vs), 1066 (s), 1039 (w), 1018 (w), 998 (w), 980 (w), 964 (w), 885 (m), 845 (w), 806 (m), 775 (w), 759 (w), 711 (w), 643 (vw). HRMS (El, pos): m/z calcd. for [M*]: 201.1001, found: 201.0993 (<10), 145.0373 (12), 101.0473 (11), 57.0699 (100), 41.0374 (39). Elemental analysis: Calcd. for $C_9H_{15}O_4N.1/18MeCN$: C, 53.77, H, 7.51, N, 7.27; found: C, 53.83, H, 7.37, N, 7.12.

Dimethyl 3,3'-thiobis(2-(((benzyloxy)carbonyl) amino)propanoate) T-n

T-n

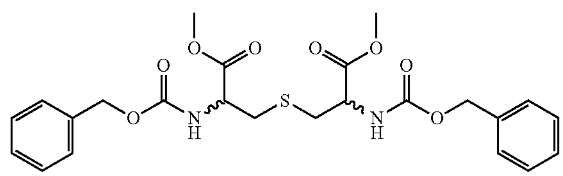

+

A-n

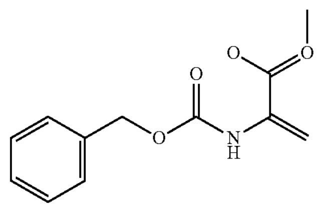

T-n was synthesized according to GP3. The sulfide was filtrated over a silica plug (8 cm, $SiO_2$, ethyl acetate) followed by ultrasonication in acetonitrile (3 mL). The resulting solution was decanted and further purified by RP-HPLC (MeCN, rt, 10 mL $m^{-1}$, $R_f$=6.30 min (T-n), $R_f$=7.00 min (A-n), $R_f$=8.00 min (NHC-thiourea)) to obtain the pure product T-n as a colourless oil which solidified over several days at room temperature to a colourless solid (82.9 mg, 168 μmol, 48%), whereas A-n was isolated as a yellow oil (53.9 mg, 229 μmol, 35%).

T-n: $^1H$ NMR (400 MHz, $CDCl_3$): δ (ppm)=7.34 (m, 10H, Ar-2/3/4-H), 5.63 (m, 2H, NH), 5.12 (s, 4H, Ar—$CH_2$), 4.58 (m, 2H, CH—$CO_2Me$), 3.75 (s, 6H, $CO_2CH_3$), 2.98 (m, 4H, S—$CH_2$—CH).13C NMR (100 MHz, $CDCl_3$): δ (ppm)=171.0 ($CO_2Me$), 155.9 (HN—C—C═O), 136.3 (Ar—C-1), 128.7 (Ar—C-3), 128.4 (Ar—C-4), 128.3 (Ar—C-2), 67.4 (Ar—$CH_2$), 53.8 (CH—$CO_2Me$), 52.9 ($CO_2Me$), 35.4 (S—$CH_2$—CH). FT-IR (ATR): ṽ $(cm^{-1})$=3332 (w), 3114 (vw), 3091 (vw), 3067 (vw), 3033 (w), 2955 (w), 2888 (vw), 2847 (vw), 1745 (s), 1716 (s), 1690 (vs), 1587 (vw), 1521 (s), 1454 (w), 1438 (m), 1407 (w), 1382 (vw), 1367 (vw), 1348 (m), 1319 (m), 1282 (m), 1237 (s), 1207 (vs), 1178 (m), 1144 (m), 1081 (m), 1058 (s), 1040 (m), 1027 (s), 1014 (s), 986 (m), 961 (w), 907 (w), 856 (w), 842 (w), 832 (w), 777 (m), 737 (s), 696 (s), 677 (vw), 636 (vw). HRMS (ESI, DCM/MeOH, pos): m/z calcd. for $[M^+]$: 1031.3025, found: 1047.2776 $[2M+K^+]$ (13), 1031.3032 $[2M+Na^+]$ (100), 527.1461 $[M+Na^+]$ (24). Elemental analysis: Calcd. for $C_{24}H_{28}O_8N_2S$: C, 57.13, H, 5.59, N, 5.55; found: C, 57.03, H, 5.64, N, 6.35.

A-n: $^1H$ NMR (600 MHz, $CDCl_3$): δ (ppm)=7.69-7.65 (m, 5H, Ar-2/3/4-H), 7.56 (s, 1H, NH), 6.56 (s, 1H, E-$CH_2$), 6.10 (d, J=1.3 Hz, 1H, Z—$CH_2$), 5.48 (s, 2H, Ar—$CH_2$), 4.14 (s, 3H, $CO_2CH_3$). $^{13}C$ NMR (150 MHz, $CDCl_3$): δ (ppm) =164.3 ($CO_2CH_3$), 153.3 (HN—C—C═O), 135.9 (Ar—C-1), 131.1 (C═$CH_2$), 128.8 (Ar—C-3), 128.6 (Ar—C-4), 128.4 (Ar—C-2), 106.2 (C═$CH_2$), 67.2 (Ar—$CH_2$), 53.1 ($CO_2CH_3$). FT-IR (ATR): ṽ $(cm^{-1})$=3705 (vw), 3412 (w), 3350 (w), 3151 (vw), 3091 (vw), 3066 (vw), 3034 (w), 2955 (w), 2899 (vw), 2851 (vw), 1803 (vw), 1739 (m), 1713 (vs), 1654 (vw), 1637 (m), 1610 (vw), 1517 (vs), 1453 (m), 1441 (s), 1377 (w), 1321 (vs), 1222 (s), 1200 (s), 1177 (m), 1084 (m), 1065 (vs), 1029 (w), 1002 (w), 990 (w), 955 (w), 896 (m), 856 (w), 847 (w), 805 (m), 770 (w), 746 (m), 697 (s), 678 (vw), 651 (vw). HRMS (El, pos): m/z calcd. for [M-$CO_2$Me*]: 176.0712 found: 176.0708 (5), 91.0540 (100). Elemental analysis: Calcd. for $C_{12}H_{13}O_4N_2$: C, H; found: C, 61.74, H, 5.61, N, 6.08.

Moreover, there are disclosed the following items:

1. A method for preparing a compound T having a thioether group from a compound D having a disulfide group, wherein the method comprises the step of: reacting the compound D in the presence of a carbene to form the compound T; wherein the compound D is a compound of the following general formula (1)

Formula (1)

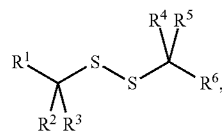

wherein $R^2$ to $R^5$ may be the same or different and are each independently selected from the group consisting of a hydrogen atom, a substituted or unsubstituted alkyl group, a substituted or unsubstituted alkenyl group, and a substituted or unsubstituted alkynyl group, wherein at least one of $R^2$ and $R^3$ is a hydrogen atom and at least one of $R^4$ and $R^5$ is a hydrogen atom; and $R^1$ and $R^6$ may be the same or different and are each independently selected from the group consisting of a substituted or unsubstituted aryl group, a substituted or unsubstituted heteroaryl group, a halogen atom, a group of the general formula (2), $—NZ^1Z^2$, $—NO_2$, —CN, $—OZ^3$, $—C(O)Z^4$, $—C(O)NZ^5Z^6$, $—COOZ^7$, and $—SO_3Z^8$, Formula (2)

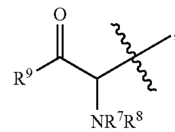

wherein $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, —$COOR^{10}$ and a peptide chain being bonded to the nitrogen atom of the $NR^7R^8$ group via its C terminus, wherein $R^{10}$ is selected from the group consisting of a substituted or unsubstituted alkyl group, a substituted or unsubstituted cycloalkyl group, a substituted or unsubstituted alkenyl group and a substituted or unsubstituted aryl group;

$R^9$ is selected from the group consisting of —$OR^{11}$ and a peptide chain being bonded to the carbon atom of the $C(O)R^9$ group via its N terminus, wherein $R^{11}$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; peptide chains, when present, may bond to each other via a peptide bond and/or via a disulfide bond and each of the peptide chains, when present, may have a disulfide bond within itself;

$Z^1$ to $Z^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; and $R^1$ to $R^6$ may bond to each other to form one or more rings.

2. The method according to item 1, wherein the amount of carbene available for converting the compound D having a disulfide group to the compound T having a thioether group is at least 1.0 equivalents in relation to the amount of disulfide groups in compound D.

3. The method according to item 1 or 2, wherein the carbene is a N-heterocyclic carbene.

4. The method according to item 3, wherein the N-heterocyclic carbene is selected from the group consisting of 1,3-bis(2,4,6-trimethylphenyl)-1,3-dihydro-2H-imidazol-2-ylidene, 1,3-bis(2,4,6-trimethylphenyl)imidazol-2-ylidene, 1,3-bis(2,6-diisopropylphenyl)imidazol-2-ylidene, 1,3-bis(2,4,6-trimethylphenyl)-4,5-dihydroimidazol-2-ylidene, 1,3-diisopropylimidazol-2-ylidene, 1,3-dimethylbenzimidazol-2-ylidene, and 1,4-dimethyl-4H-1,2,4-triazol-5-ylidene.

5. The method according to any one of items 1 to 4, wherein the compound T is a compound of the following general formula (3)

Formula (3)

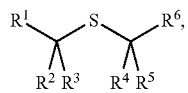

wherein $R^2$ to $R^5$ may be the same or different and are each independently selected from the group consisting of a hydrogen atom, a substituted or unsubstituted alkyl group, a substituted or unsubstituted alkenyl group, and a substituted or unsubstituted alkynyl group, wherein at least one of $R^2$ and $R^3$ is a hydrogen atom and at least one of $R^4$ and $R^5$ is a hydrogen atom; and $R^1$ and $R^6$ may be the same or different and are each independently selected from the group consisting of a substituted or unsubstituted aryl group, a substituted or unsubstituted heteroaryl group, a halogen atom, a group of the general formula (2), —$NZ^1Z^2$, —$NO_2$, —CN, —$OZ^3$, —$C(O)Z^4$, —$C(O)NZ^5Z^6$, —$COOZ^7$, and —$SO_3Z^8$, Formula (2)

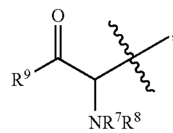

wherein $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, —$COOR^{10}$ and a peptide chain being bonded to the nitrogen atom of the $NR^7R^8$ group via its C terminus, wherein $R^{10}$ is selected from the group consisting of a substituted or unsubstituted alkyl group, a substituted or unsubstituted cycloalkyl group, a substituted or unsubstituted alkenyl group and a substituted or unsubstituted aryl group;

$R^9$ is selected from the group consisting of —$OR^{11}$ and a peptide chain being bonded to the carbon atom of the $C(O)R^9$ group via its N terminus, wherein $R^{11}$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; peptide chains, when present, may bond to each other via a peptide bond and/or via a disulfide bond and each of the peptide chains, when present, may have a disulfide bond within itself;

$Z^1$ to $Z^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; and $R^1$ to $R^6$ may bond to each other to form one or more rings.

6. The method according to any one of items 1 to 5, wherein $R^1$ and $R^6$ are each independently selected from a substituted or unsubstituted aryl group, a substituted or unsubstituted heteroaryl group, a group of the general formula (2), and —$COOZ^7$.

7. The method according to any one of items 1 to 6, wherein each of $R^2$ to $R^5$ is a hydrogen atom and $R^1$ and $R^6$ may bond to each other to form one or more rings.
8. The method according to any one of items 1 to 7, wherein compound D is a polypeptide having one or more disulfide bonds or another compound having an oligomeric, polymeric, macrocyclic, or cage structure and having one or more disulfide bonds, wherein the polypeptide is preferably a precursor compound of a lantibiotic.
9. The method according to any one of items 1 to 8, wherein the compound D has from 1 to 20 disulfide groups.
10. The method according to item 9, wherein from 25% to 100% of the disulfide groups of compound D are converted into thioether groups in the compound T.
11. The method according to any one of items 1 to 10, wherein the compound T is a polypeptide, preferably a lantibiotic, or another compound having an oligomeric, polymeric, macrocyclic, or cage structure.
12. The method according to any one of items 1 to 11, wherein the compound D is reacted in the presence of a solvent, wherein the solvent is preferably selected from one or more of the group consisting of 1,4-dioxane, diethyl ether, water, ionic liquids, halogenated solvents, DMSO, THF, DMF, acetonitrile, toluene, n-hexane, methanol, ethanol, and isopropanol.
13. The method according to item 12, wherein the amount of solvent is from 1.0 L to 1000 L per 1.0 mole of compound D.
14. The method according to any one of items 1 to 13, wherein the step of reacting the compound D is carried out at a temperature from 0° C. to 80° C. for 30 s to 10 d.
15. The method according to any one of items 1 to 14, wherein the carbene is obtained from the corresponding protonated salt and a base, wherein the base is preferably selected from the group consisting of a hydride, a carbonate, an alcoholate, DBU, alkali HMDS, and LDA.

The invention claimed is:

1. A method for preparing a compound T having a thioether group from a compound D having a disulfide group, wherein the method comprises the step of:

reacting the compound D in the presence of a carbene to form the compound T;

wherein the compound D is a compound of the following general formula (1) and the compound T is a compound of the following general formula (3)

Formula (1)

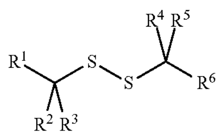

Formula (3)

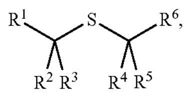

wherein $R^2$ to $R^5$ are each a hydrogen atom; and $R^1$ and $R^6$ may be the same or different and are each independently selected from the group consisting of a substituted or unsubstituted aryl group, a substituted or unsubstituted heteroaryl group, a group of the general formula (2), and —$COOZ^7$, Formula (2)

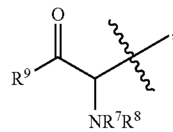

wherein $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, and —$COOR^{10}$, wherein $R^{10}$ is selected from the group consisting of a substituted or unsubstituted alkyl group, a substituted or unsubstituted cycloalkyl group, a substituted or unsubstituted alkenyl group and a substituted or unsubstituted aryl group;

$R^9$ is selected from the group consisting of —$OR^{11}$, wherein $R^{11}$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$Z^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group; and $R^1$ and $R^6$ may bond to each other to form one or more rings; and wherein the carbene is an N-heterocyclic carbene selected from the group consisting of 1,3-bis(2,4,6-trimethylphenyl)-1,3-dihydro-2H-imidazol-2-ylidene, 1,3-bis(2,4,6-trimethylphenyl) imidazol-2-ylidene, 1,3-bis(2,6-diisopropylphenyl)-imidazol-2-ylidene, 1,3-bis(2,4,6-trimethylphenyl)-4,5-dihydroimidazol-2-ylidene, 1,3-diisopropylimidazol-2-ylidene, 1,3-dimethylbenzimidazol-2-ylidene, and 1,4-dimethyl-4H-1,2,4-triazol-5-ylidene.

2. The method according to claim 1, wherein the amount of carbene available for converting the compound D having a disulfide group to the compound T having a thioether group is at least 1.0 equivalents in relation to the amount of disulfide groups in compound D.

3. The method according to claim 1, wherein the compound D is reacted in the presence of a solvent.

4. The method according to claim 3, wherein the amount of solvent ranges from 1.0 L to 1000 L per 1.0 mole of compound D.

5. The method according to claim 1, wherein the step of reacting the compound D is carried out at a temperature ranging from 0° C. to 80° C. for 30 seconds to 10 days.

6. The method according to claim 1, wherein the carbene is obtained from the corresponding protonated salt and a base.

7. The method according to claim 6, wherein the base is selected from the group consisting of a hydride, a carbonate, an alcoholate, DBU, alkali HMDS, and LDA.

8. The method according to claim 3, wherein the solvent is selected from one or more of the group consisting of 1,4-dioxane, diethyl ether, water, ionic liquids, halogenated solvents, DMSO, THF, DMF, acetonitrile, toluene, n-hexane, methanol, ethanol, and isopropanol.

* * * * *